(12) United States Patent
Riviere et al.

(10) Patent No.: US 7,517,693 B2
(45) Date of Patent: Apr. 14, 2009

(54) METHOD AND APPARATUS FOR DETERMINING A MOLECULAR DESCRIPTOR OF ABSORPTION FOR A CANDIDATE COMPOUND

(75) Inventors: Jim E. Riviere, Raleigh, NC (US); Xin-Rui Xia, Durham, NC (US); Ronald E. Baynes, Garner, NC (US); Nancy A. Monteiro-Riviere, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 356 days.

(21) Appl. No.: 10/382,209

(22) Filed: Mar. 5, 2003

(65) Prior Publication Data
US 2003/0180954 A1   Sep. 25, 2003

Related U.S. Application Data

(60) Provisional application No. 60/361,926, filed on Mar. 5, 2002.

(51) Int. Cl.
 G01N 21/00 (2006.01)
 G01N 21/75 (2006.01)
 G01N 21/77 (2006.01)
(52) U.S. Cl. ............... 436/164; 422/68.1; 422/101; 436/169; 73/38; 73/64.47
(58) Field of Classification Search ............... 436/5, 436/164, 169; 702/19, 22; 422/68.1, 101; 73/38, 64.47
See application file for complete search history.

(56) References Cited

U.S. PATENT DOCUMENTS

| | | | | |
|---|---|---|---|---|
| 4,093,515 A | * | 6/1978 | Kolobow | 435/2 |
| 4,812,407 A | | 3/1989 | Buchmann et al. | 435/291 |
| 4,931,498 A | * | 6/1990 | Pidgeon | 525/54.1 |
| 4,960,415 A | * | 10/1990 | Reinmuller | 604/890.1 |
| 5,492,943 A | | 2/1996 | Stempel | 523/111 |
| 6,360,588 B1 | | 3/2002 | Ross et al. | 73/38 |
| 6,395,656 B1 | * | 5/2002 | Jin et al. | 442/159 |
| 6,829,540 B1 | * | 12/2004 | Pidgeon et al. | 702/22 |

* cited by examiner

*Primary Examiner*—Jill Warden
*Assistant Examiner*—Keri A Moss
(74) *Attorney, Agent, or Firm*—Jenkins, Wilson, Taylor & Hunt, P.A.

(57) ABSTRACT

A method of determining a molecular descriptor of absorption for a candidate compound is disclosed. The method includes: providing a test solution comprising one or more candidate compounds; contacting the test solution with a simulated biological membrane to partition the one or more candidate compounds into the membrane detecting the presence or amount of the one or more candidate compound in the membrane at one or more permeation times; and determining a molecular descriptor of absorption using the presence or amount of the one or more candidate compound in the membrane at the one or more permeation times. In one aspect the invention provides a skin-imitating membrane, and one or more percutaneous absorption parameters are determined. In another aspect the membrane is disposed on a fiber. In another aspect the test solution is contacted with two or more simulated biological membranes to partition the one or more candidate compounds into the membranes.

29 Claims, 10 Drawing Sheets

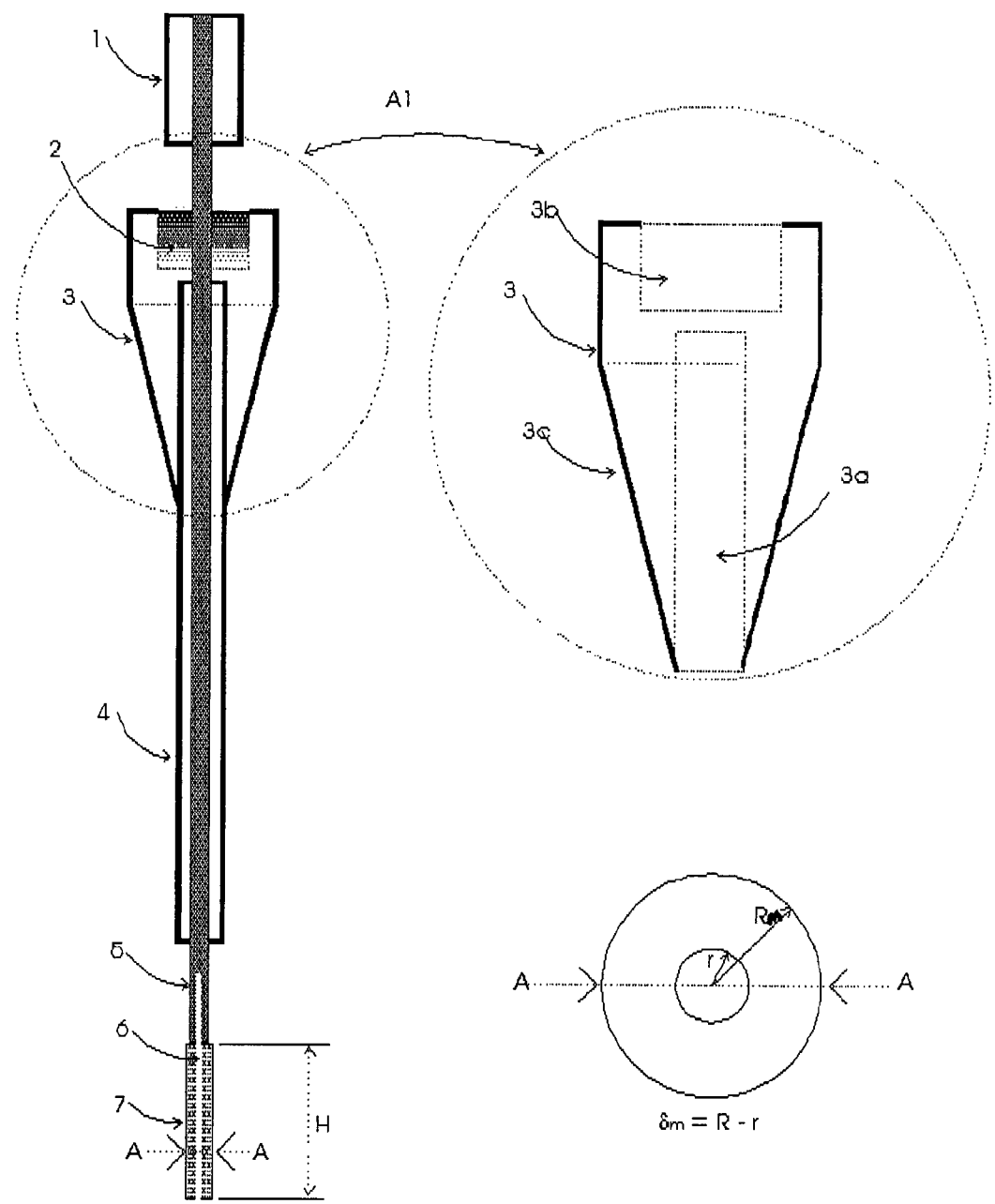
FIG. 3 Membrane Coated Fiber and Assembly

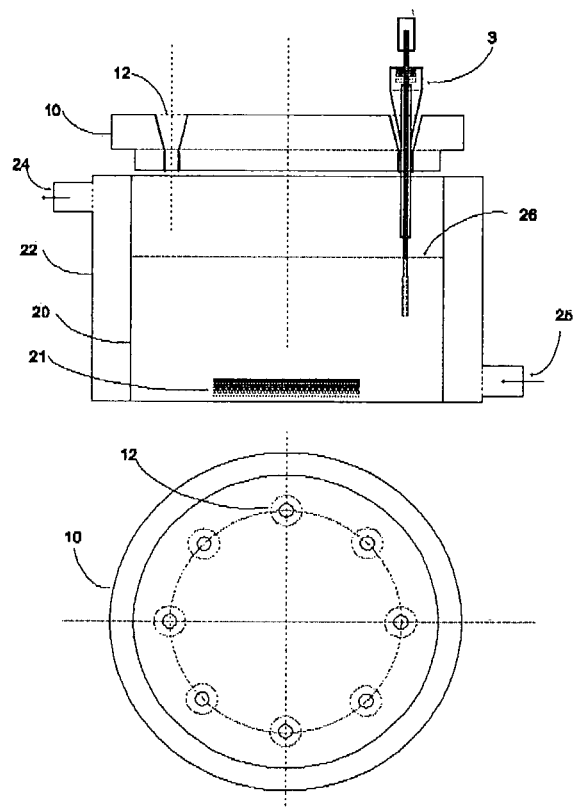
FIG. 4 Container with A Special Needle Holding Cap and Water Jacket
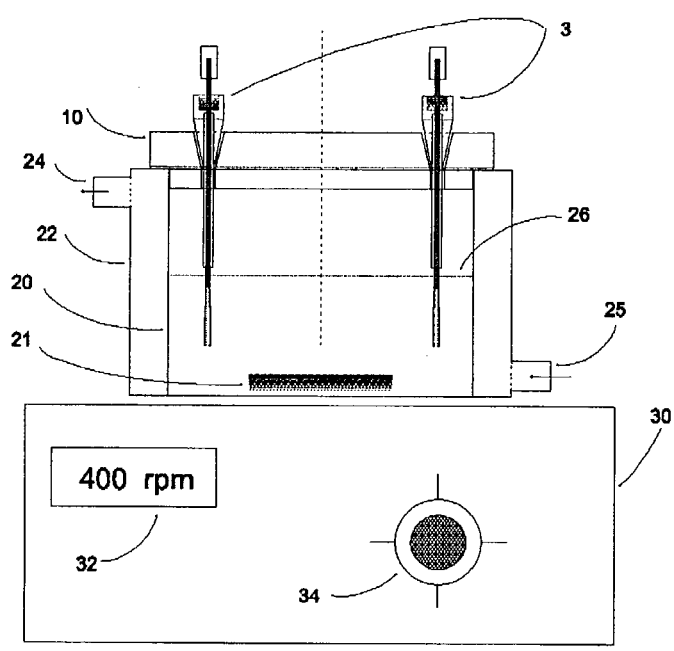
FIG. 5 Absorption Setup with Coated Fibers.

METHOD AND APPARATUS FOR DETERMINING A MOLECULAR DESCRIPTOR OF ABSORPTION FOR A CANDIDATE COMPOUND

CROSS REFERENCE TO RELATED APPLICATIONS

This application is based on and claims priority to U.S. Provisional Application Ser. No. 60/361,926, filed Mar. 5, 2002, and entitled METHOD AND APPARATUS FOR DETERMINING A MEMBRANE ABSORPTION PARAMETER FOR A CANDIDATE COMPOUND, herein incorporated by reference in its entirety.

TECHNICAL FIELD

The present invention relates to a method and apparatus for assessment of membrane absorption, and in one embodiment to a method and apparatus that employs a fiber coated with a skin-imitating membrane and an absorption container for rapid assessment of percutaneous absorption.

BACKGROUND ART

Assessment of percutaneous absorption is of importance to many industrial and scientific fields. The principal application areas are the development of (i) transdermal drug delivery devices to deliver drugs across skin to treat ether local (skin) or systemic diseases; (ii) dermatological formulations in medicine, pharmacy and cosmetics; (iii) safety assessment of cosmetics; and (iv) risk assessment of environmental or occupational hazards. Great efforts have been devoted to develop experimental approaches to measure percutaneous absorption. To date, most of the data on percutaneous absorption have been gained in vitro by diffusion chamber experiments, while in vivo data are commonly obtained from animal experiments via biomonitoring. Bronaugh, R. L. (ed.), Percutaneous absorption: drugs-cosmetics-mechanisms-methodology. 1999, Marcel Dekker, Inc. New York, pp. 123; Schaefer H. Redelmeier T. E. (eds), Skin barrier: principles of percutaneous absorption. 1996, S. Karger AG, Basel, Switzerland, p. 310.

A key function of skin is to provide a barrier that protects the body from foreign substances. Any drug or chemical agent must penetrate the skin's barrier to act ether locally or systemically. Decades of study have established that skin comprises two layers, epidermis and dermis. The epidermis has no capillary blood flow but is made up of several layers of enzymatically active cells, while the dermis in the skin inner layer contains the capillary network that transports the drug or chemical agent to the systemic circulation. The outmost layer of the epidermis is stratum corneum, which comprises layers of keratinized dead cells surrounded by intercellular lipid. Stratum corneum behaves like a passive diffusion barrier. It is responsible for limiting the passage of exogenous chemicals across the skin into the systemic circulation. Agatonovic-Kustrin, S., et al., *J. Pharm. Biomed. Anal.* 26(2001)241-254.

It is difficult to prepare a large quantity of human skin epidermal membranes for industrial and scientific laboratories. It is conventional practice to use polymeric membranes as skin-imitating barriers to study percutaneous absorption. Skin-imitating membranes differ advantageously from human skin epidermis due to their ready availability, uniformity, tensile strength and chemical purity. Feldstein, M. M., et al., *J. Controlled. Release* 52 (1998)25-40; Baynes, R. E., et al., *Toxicology Industrial Health* 16(2000) 225-233. Silastic membranes are the most widely used skin-imitating membranes because of their high permeability comparable with human stratum corneum; and its properties can be modified to simulate skin.

There are mainly two kinds of diffusion chambers currently found in the art, Franz diffusion cell (A) and flow-through diffusion cell (B) as shown in FIG. 1. In these diffusion cells the membrane (a) is placed between two chambers, donor (b) and receptor (c), and the compound in question diffuses from the donor phase through the membrane into the receptor phase. In Franz diffusion cell samples are withdrawn periodically from the receptor phase (g) and analyzed to measure the penetration flux. In the flow-through cell the compounds passing through the membrane are carried away by the receptor fluid flowing beneath the membrane undersurface to be collected in discrete volumes at a remote location. The advantages of the flow-through cell are allowing automatic sampling; maintaining sink conditions since the receptor fluid is replaced continuously, and mimicking the subcutaneous blood flow by the movement of the receptor fluid beneath the undersurface of the membrane. Bronaugh, R. L. (ed.), Percutaneous absorption: drugs-cosmetics-mechanisms-methodology. 1999, Marcel Dekker, Inc. New York, pp. 123; Schaefer H. Redelmeier T. E. (eds), Skin barrier: principles of percutaneous absorption. 1996, S. Karger AG, Basel, Switzerland, p. 310.

The basic compartments of a diffusion cell are illustrated in FIG. 2. The concentration of a given compound is $C^o$ in the bulk solution of the donor phase. In the vicinity of the membrane the concentration of the compound is lower than the bulk solution because of the absorption by the membrane, which results in a concentration gradient ($C^o \rightarrow C_{dx}$) in the boundary layer between the membrane and the donor phase. There is also a concentration gradient ($C_{rx} \rightarrow C_r$) in the boundary layer between the membrane and the receptor phase because the compound passing through the membrane is carried away by the receptor fluid.

The surface concentration in the donor phase ($C_{dx}$) is a critical concentration available for the percutaneous absorption. It is determined by the bulk concentration ($C^o$), hydrodynamic agitation, the mass of the compound, and the temperature and viscosity of the solution. At steady-state partition equilibrium is established on both sides of the membrane ($K_{md} = C_{md}/C_{dx}$, $K_{mr} = C_{mr}/C_{rx}$). The surface concentration in the receptor phase ($C_{rx}$) is also a relevant concentration for the penetration. It is this available concentration that determines the diffusion rate into the receptor phase rather than the concentration in the membrane.

There are several problems in current diffusion cells for in vitro percutaneous absorption. First of all, only trace amounts of compound penetrate the membrane into the receptor phase. A very sensitive Liquid Scintillation Counting (LSC) instrument is required. Thus, chemical agents of interest must often be radiolabeled, and often only one chemical can be studied at a time. This makes the current assessment of percutaneous absorption very expensive and time consuming. Additionally, millions of chemicals in varieties of industrial and environmental matrices are needed to be screened for percutaneous absorption, and many more formulations need to be screened for better drugs, pharmaceuticals, and cosmetics.

Moreover, current techniques using radiolabeled chemical agents cannot handle multiple chemicals and their combinations. Conventional diffusion cells are also designed to mimic an in vivo situation, but experiments are not performed with rigorous compliance to the diffusion laws. The boundary layers in the donor phase and receptor phase are not considered. The diffusion coefficient in the membrane calculated from the absorption flux is only an apparent diffusion coefficient that includes contributions of diffusion resistances from the boundary layers and the membrane. Therefore, the experimental data obtained are only useful to predict the in vivo situation under similar experimental conditions; it cannot be simply interpreted by diffusion laws and cannot be directly analyzed and discussed with kinetic and thermodynamic parameters. For example, the absorption of lipophilic compounds is controlled by the boundary layer diffusion. The absorption rate will be affected by hydrodynamic agitation, solution viscosity and temperature rather than by the structure of the membrane. Misleading interpretation of the experimental data would occur if the existence of the boundary layers is not considered. The present invention addresses these and other problems in the art.

SUMMARY OF THE INVENTION

A method of determining a molecular descriptor of absorption for a candidate compound is disclosed. In one embodiment, the method comprises: (a) providing a test solution comprising one or more candidate compounds; (b) contacting the test solution with one or more simulated biological membranes to partition the one or more candidate compounds into the membrane; (c) detecting the presence or amount of the one or more candidate compound in the membrane at one or more permeation times; and (d) determining a molecular descriptor of absorption using the presence or amount of the one or more candidate compound in the membrane at the one or more permeation times.

In another embodiment, a method of determining a molecular descriptor of absorption for a candidate compound comprises: (a) providing a test system comprising: (i) a membrane assembly comprising one of a fiber and a simulated biological membrane membrane disposed thereon and a tube and a simulated biological membrane disposed therein; and (ii) a container comprising a cover having one or more apertures disposed therein, the one or more apertures adapted to receive the membrane assembly; (b) providing a test solution in the container, the test solution comprising one or more candidate compounds, wherein the one or more candidate compounds are present in a known concentration; (c) contacting the test solution with the simulated biological membrane by placing the membrane assembly into an aperture of the container cover, whereby the one or more candidate compounds partition into the membrane; (d) detecting the presence or amount of the one or more candidate compounds in the membrane at one or more permeation times; and (e) determining a molecular descriptor of absorption using the presence or amount of the one or more candidate compounds in the membrane at the one or more permeation times.

Optionally, the method comprises determining a plurality of molecular descriptors of absorption. The test solution can comprise a plurality of test compounds, e.g. a plurality of different test compounds. Optionally, the method can comprise contacting the test solution with two or more simulated biological membranes to partition the one or more candidate compounds into the membranes. The two or more simulated biological membranes can be the same or different. The test solution can be stirred during the contacting of step (b). The membrane can be configured by one of disposing the membrane on a fiber or disposing the membrane within a tube. Optionally, the membrane has a constant thickness along the fiber. The simulated biological membrane can simulates a biological barrier or membrane selected from the group consisting of subcellular, cellular, oral/mucosal, gastrointestinal, blood-brain, respiratory-lung, nasal, ocular, subconjuctival, and skin. The detecting is done by gas chromatography or high performance liquid chromatography, such as by injecting the fiber into a gas chromatograph or high performance liquid chromatograph. Optionally, a molecular descriptor of absorption can be compared to a reference molecular descriptor of absorption.

A system for determining a molecular descriptor of absorption for a candidate compound is also disclosed. In one embodiment, the system comprises: (a) a membrane assembly comprising one of a fiber and a simulated biological membrane membrane disposed thereon and a tube and a simulated biological membrane disposed therein; and (b) a container comprising a cover having one or more apertures disposed therein, the one or more apertures adapted to receive the membrane assembly.

The membrane can have a constant thickness along the fiber. The one or more apertures can be located at a fixed distance from a center point of the container. The fixed distance can comprise a fixed radius.

The system can comprise a stirring platform adapted to receive the container and a stir bar for use therewith. The system can comprise an apparatus for quantitatively analyzing the presence or amount of one or more candidate compounds in the membrane. The apparatus for quantitative analysis can be a gas chromatograph or a high performance liquid chromatography apparatus.

A method of assessing susceptibility of a candidate compound to absorption into a biological membrane is also disclosed. In one embodiment, the method comprises: (a) obtaining a molecular descriptor of absorption for a candidate compound in one or more simulated biological membranes, wherein the one or more simulated biological membranes simulate the biological membrane; (b) comparing the molecular descriptor of absorption to a reference molecular descriptor of absorption; and (c) assessing susceptibility to absorption into the biological membrane based on the comparing of step (b).

The molecular descriptor of absorption can be compared to a plurality of reference molecular descriptors of absorption. A plurality of molecular descriptors of absorption for the candidate compound can be obtained. The plurality of molecular descriptors of absorption can be compared to a plurality of reference molecular descriptors of absorption. The one or more simulated biological membranes can simulate a biological barrier or membrane selected from the group consisting of subcellular, cellular, oral/mucosal, gastrointestinal, blood-brain, respiratory-lung, nasal, ocular, subconjuctival, and skin.

A computer-readable medium having stored thereon instructions for assessing susceptibility of a candidate compound to absorption into a biological membrane is also disclosed.

A system for assessing susceptibility of a candidate compound to absorption into a biological membrane is also disclosed. In one embodiment, the system comprises: (a) an input for obtaining a molecular descriptor of absorption for a candidate compound in one or more simulated biological membranes, wherein the one or more simulated biological membranes simulate the biological membrane; (b) a database for comparing the molecular descriptor of absorption to a reference molecular descriptor of absorption; and (c) a comparator program for assessing susceptibility to absorption into the biological membrane based on the comparing of step (b). Optionally, the system can comprise a database for comparing the molecular descriptor of absorption to a plurality of reference molecular descriptors of absorption. The system can comprise an input for obtaining a plurality of molecular descriptors of absorption for the candidate compound. The system can comprise a database for comparing the plurality of molecular descriptors of absorption to a plurality of reference molecular descriptors of absorption.

Also disclosed is a computer-readable medium having stored thereon a data structure, comprising: (a) a first data field containing data representing a type of a molecular descriptor of absorption; and (b) a second data field containing data representing a value of a molecular descriptor of absorption.

BRIEF DESCRIPTION OF THE DRAWINGS

FIG. 3 depicts the membrane-coated fiber assembly of the present invention.

FIG. 4 depicts a system of the present invention, including container with needle holding cap and water jacket.

FIG. 5 depicts a system of the present invention, including absorption setup with coated fibers.

DETAILED DESCRIPTION OF THE INVENTION

Figure 1:
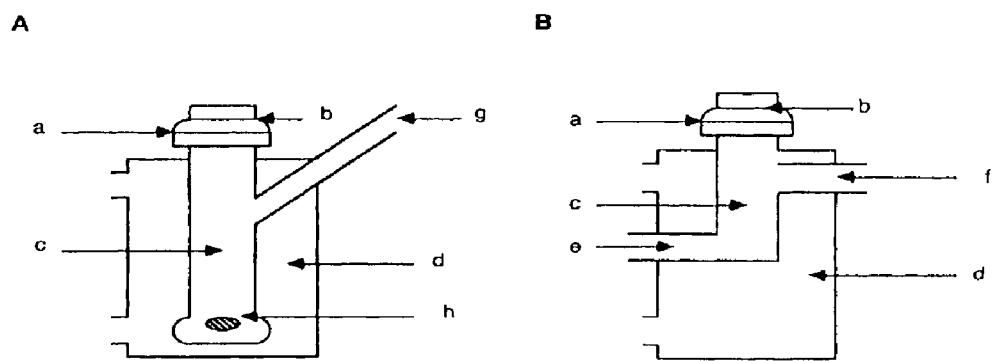
FIGS. 1A and 1B are diagrammatic representations of the Franz diffusion cell and flow-through cell, respectively. Cell components are as follows: (a) membrane; (b) donor compartment; (c) receptor compartment; (d) water jacket; (e) receptor inlet; (f) receptor outlet; (g) receptor sampling port; (h) magnetic stir bar.

Current techniques for assessment of percutaneous absorption are time consuming. Current techniques also typically require radiolabeled chemical agents and study only one chemical at a time. The present invention overcomes these obstacles. In one embodiment, a skin-imitating membrane is coated on a section of inert fiber to be used as a permeation membrane. The membrane-coated fiber (MCF) is immersed in the donor phase to partition the compounds into the membrane. At given permeation times the membrane-coated fiber is transferred into the injection port of a gas chromatograph or a high-performance liquid chromatograph to desorb the compounds for quantitative and qualitative analyses. Many compounds can be studied at a single run because of the high separation power of the chromatographic techniques. This feature is useful to study the synergistic effect of multiple chemicals and their combinations on percutaneous absorption. Expensive radiolabeled compounds are not required.

This membrane-coated fiber characterizes a half compartment of the conventional diffusion chamber, which allows more detailed permeation kinetics to be investigated. A theoretical model is provided and describes the permeation processes of the skin-imitating membrane coated fiber. An absorption container is designed to incorporate the membrane-coated fiber to meet the requirements of the theoretical derivation for percutaneous absorption.

Further, physical chemical interactions, characteristics or factors that significantly alter in vivo dermal absorption after exposure in a complex chemical mixture, are primarily related to solute/solvent, solute/solute, solvent/membrane or solute/membrane interactions that are detectable in an appropriately optimized and parameterized in vitro system. In one embodiment, the present invention provides an experimental approach that defines these interactions in terms of molecular descriptors that make the results applicable to other pharmaceutical and toxicological problems.

An aspect of the present invention is to identify specific chemical mixture interactions that result in significant changes to in vivo dermal absorption. Thus, provided is a generally applicable in vitro experimental framework that allows chemical mixture interactions to be classified by mechanisms that significantly modulate absorption. Quantitative Structure Activity Relationship (QSAR) methods are employed to describe dermal absorption profiles in the well-established and validated isolated perfused porcine skin flap (IPPSF) model to thereby link chemical mixture induced changes in molecular descriptors (e.g, $R_2$, $\pi$, $\alpha$, $\beta$, V and L, which are defined herein below) determined in a membrane-coated fiber (MCF), directly to changes in percutaneous absorption profiles from perfused skin that are predictive of human in vivo dermal absorption.

Thus, in one embodiment, the MCF approach is employed to experimentally measure multiple partition coefficients (log $K_{m/s}$) between study chemicals and a number of physical and chemically diverse membranes (m) in biologically relevant solvent(s) systems. The log $K_{m/s}$ is scaled to the molecular descriptors by specific intermolecular forces defined by a linear solvation energy equation. These molecular descriptors also parameterize the IPPSF model, providing the link between the MCF and IPPSF systems. Multiple MCFs are calibrated using compounds with known values of the molecular descriptors with multiple solvation energy equations describing log $K_{m/s}$. These calibrated MCFs are then used as a reference system to determine the molecular descriptors for any study chemicals of toxicological significance.

To assess mixture or solvent effects, log $K_{m/s}$ are determined in the mixture or solvent solutions using the calibrated MCFs. Change in a chemical's log $K_{m/s}$ relative to the reference system's, reflective of mixture effects, is quantitated as apparent change ($\delta$) in a chemical's molecular descriptors from reference control values. This provides an experimental approach for quantitative assessment of chemical mixture exposure scenarios. Since the IPPSF's in vivo absorption estimates are parameterized in terms of the molecular descriptors, $\delta$ values can be linked to the IPPSF to predict changes in absorption profiles.

A strength of the IPPSF model is its sensitivity to biological effects. Using nonlinear mixed effect pharmacokinetic modeling, changes in IPPSF flux profiles due to biological modifiers can be assessed using independent markers of biological activity (e.g. inflammatory cytokine IL-8 release, changes in infrared spectra in stratum corneum determined using FTIR) and then integrated into the model as explanatory or concomitant variables. This approach allows a direct identification of mixture or solvent effects that would be expected to significantly alter in vivo disposition.

I. Candidate Compounds

The term "candidate compound" is meant to refer to any compound wherein characterization of the compound's susceptibility to percutaneous absorption is desirable. Exemplary candidate compounds include xenobiotics such as drugs and other therapeutic agents; carcinogens and environmental pollutants; pesticides; and endobiotics such as steroids, fatty acids and prostaglandins. Other representative candidate compounds, including those employed for calibration, are disclosed in the Examples. The terms "solute", "penetrant", and/or "solute/penetrant" can be used herein interchangeably with the term "candidate compound".

Some of the candidate compounds screened in accordance with the method of the present invention are contemplated to be useful in the treatment of warm-blooded vertebrates. Therefore, the invention concerns mammals and birds.

Contemplated is the treatment of mammals such as humans, as well as those mammals of importance due to being endangered (such as Siberian tigers), of economical importance (animals raised on farms for consumption by humans) and/or social importance (laboratory animals such as but not limited to mice, rats, rabbits, cats, dogs, and monkeys, and animals kept as pets or in zoos) to humans, for instance, carnivores other than humans (such as cats and dogs), swine (pigs, hogs, and wild boars), ruminants (such as cattle, oxen, sheep, giraffes, deer, goats, bison, and camels), and horses. Also contemplated is the treatment of birds, including the treatment of those kinds of birds that are endangered, kept in zoos, as well as fowl, and more particularly domesticated fowl, i.e., poultry, such as turkeys, chickens, ducks, geese, guinea fowl, and the like, as they are also of economical importance to humans. Thus, contemplated is the treatment of livestock, including, but not limited to, domesticated swine (pigs), ruminants, horses, poultry, and the like.

II. General Considerations for Quantitative Structure Permeability Studies

There have been numerous and well documented approaches to quantitate the rate and extent of percutaneous absorption using quantitative structure permeability relationships (QSPR) for chemical transport through skin. See Moss et al., 2002 (review); Hansch and Dunn (1972). Additional dermal work was "launched" by the compilation of Flynn (1990) of the permeability coefficients (Kp) for 94 compounds primarily in vitro through human skin from 15 different sources in the art. The first analysis of this data (Potts and Guy, 1992) quantified permeability in a QSPR equation as:

$$\text{Log } K_p = 0.71 \log K_{o/w} - 0.0061 \, MW - 6.3 \; (R^2 = 0.67) \quad \text{(Eq. 1)}$$

In their analysis, Potts and Guy indicated that there was up to 30% variability in the heterogeneous data sets analyzed, making an $R^2$ of 0.7 reasonable. This was largely due to the inherent variability in diffusion cell experiments confounded by the fact that the data were generated by some 15 different investigators in the art.

E I Tayar et al. (1991) analyzed subsets of compounds from the Flynn dataset and described a correlation with a hybrid parameter $\Delta \log K_{oct-hep}$ ($K_{oct/water} - K_{heptane/water}$), which provides an estimate of the hydrogen bond donor acidity of the solutes. Pugh and Hadgraft (1994) analyzed this same data set using an ab initio approach using up to 17 fragments based on various molecular substructures and features and achieved a comparable correlation to Potts and Guy. This study identified a number of outlier compounds that were also identified by other workers subsequently analyzing this dataset.

Potts and Guy (1995) further investigated the role of hydrogen bonding on a subset of 37 non-electrolytes from the Flynn compounds that yielded the following relationship, which shed light on the importance of hydrogen bonding parameters on the mechanism of skin permeation:

$$\text{Log } K_p = 0.0256 \, MV - 1.72 \Sigma \alpha_2^H - 3.93 \Sigma \beta_2^H - 4.85$$
$$(R^2 = 0.94) \quad \text{(Eq. 2)}$$

where MV is the molecular volume (cm³/mole), $\Sigma \alpha_2^H$ is the solute hydrogen bond acidity and $\Sigma \beta_2^H$ is the solute hydrogen bond basicity. Others have employed a compound's melting point as a measurable molecular descriptor (Barratt, 1995).

Abrahams et al. (1995, 1999) attempted to generalize these solute-solvent interactions for permeability through biological membranes, including skin, in the context of linear free energy or solvation energy relationships that expressed as basic solvation equations:

$$\text{Log } K_p = c + rR_2 + s\pi_2^H + a\Sigma\alpha_2^H + b\Sigma\beta_2^H + vV_x \text{ or alternatively}$$

$$\text{Log } K_p = c + rR_2 + s\pi_2^H + a\Sigma\alpha_2^H + b\Sigma\beta_2^H + l \log L^{16} \quad \text{(Eq. 3)}$$

where $R_2$ is the excess molar fraction calculated from a solute's refractive index, $\pi_2^H$ is a dipolarity/polarizability constant, $\Sigma\alpha_2^H$ and $\Sigma\beta_2^H$ are effective hydrogen bonding acidity and basicity parameters, $V_x$ is the McGowan characteristic molecular volume that can be calculated from an appropriate algorithm, and log $L^{16}$ is the solute gas-hexadecane partition coefficient. Log $L^{16}$ has been used for the gas-liquid phase while $V_x$ is used for liquid-liquid and liquid-membrane phases. The molecular descriptors are properties of the compounds and assumed not to change in different gas and liquid transport processes. Solvation equations such as these link molecular descriptors to transport related properties such as membrane permeability or partition coefficients, where solute-solvent and solute-membrane interactions dominate. Using this approach to predict the in vitro skin permeability coefficient, Abraham's analysis of the Flynn dataset resulted in a $R^2$ of 0.96 for a series of 53 compounds.

III. Molecular Descriptors

In one embodiment the present invention quantifies the relationship between experimentally determined partition coefficients and a chemical's molecular descriptors using the MCF technique to measure a series of partition coefficients in different membranes of diverse physical chemical properties. The isolated perfused porcine skin flap system (IPPSF) described herein provides estimates of dermal absorption. The IPPSF model has been shown to correlate to human in vivo absorption and has been shown to be sensitive to biological modifiers such as chemical induced irritation or vascular activity. Once the MCF systems are calibrated, the effects of a specific chemical mixture component can be tested in these systems. The MCF technique is an experimental system closer to the basic properties embodied in a theoretical QSPR analysis. The IPPSF moves the in vitro skin model closer to the biological functionality inherent to in vivo studies, without the presence of confounding systemic factors and procedural or ethical hurdles inherent to conducting both animal and human trials.

Linear salvation energy relationships can be used to predict skin absorption and to make observations that can be generalized across molecules of very different physical chemical properties, as well as levels of model systems. QSPR studies have defined a set of molecular descriptors, including, for example, descriptors that related to hydrogen bonding. It is well known that hydrophobicity of a compound plays a very important part in partitioning, permeation, and deposition in a biological system. Molecular volume, often roughly estimated as molecular weight in early analyses, is also an important geometric factor of the compound. In Abraham's linear solvation energy relationship, $V_x$ and log L were used alternatively for solution-membrane and gas-membrane systems (Eq. 3). Abraham (1999) believed that solute cavity volume ($V_x$) and dispersion interactions are highly correlated and cannot be separated. Theoretically, geometric size (intrinsic volume) and hydrophobicity (dispersion force) of a compound are two distinct molecular properties. For example, $HO[CH_2CH_2O]_4H$ and $CH_3[CH_2]_{10}CH_3$ have similar chain lengths, but their hydrophobicities are significantly different.

Contributions from both geometric size and hydrophobicity are included in the linear solvation energy equation employed herein. Intrinsic molecular volume is used for the molecular volume term that can be calculated for any compound, such as by using the computer program MOLSV (QCPE, Indiana University, Bloomington, Ind., United States of America). The hydrophobicity term is the partition coefficient of a chemical between gas phase and a hydrophobic MCF (without polar type or H-bonding capacity) that is expected to be similar to the gas-hexadecane partition coefficient available in the art. Thus, the basic linear solvation energy equation is constructed as:

$$\log K_{m/s} = c + rR + s\pi + a\alpha + b\beta + vV + l\log L \quad (\text{Eq. 4})$$

The variables [R, π, α, β, V and L] are molecular descriptors of the solute. Each of the solute descriptors represents the strength of the corresponding intermolecular force of the solute. The values of these descriptors are available in the art for the calibration compounds disclosed in the Examples below.

log $K_{m/s}$ is the partition coefficient of a solute between the membrane and solvent determined by the MCF technique.

R is an excess molar refraction that can be calculated from refractive index.

π is the effective solute dipolarity and polarizability.

α is the effective solute H-bond acidity, a summation of acidity from all H-bonds of the solute.

β is the effective solute H-bond basicity, a summation of basicity from all H-bonds of the solute.

V is the intrinsic volume of solute that can be calculated (such as by using the MOLSV software package)

L is the solute gas-hexadecane partition coefficient at 25° C.

The constants [c, r, s, a, b, v and l] are parameters of the membrane/solvent system for which log $K_{m/s}$ is being measured. Each of the system parameters represents the strength of the corresponding intermolecular force of the system. These strength coefficients essentially scale the contribution of each molecular descriptor in determining the log $K_{m/s}$ to the specific fiber being studied. These system constants can be obtained through data regression of specifically designed experimental measurement by the MCF technique.

The r-constant shows the tendency of the system to interact with solutes through π*- and n-electron pairs. Usually the r-coefficient is positive, but for phases that contain fluorine atoms, the r-coefficient can be negative.

The s-constant gives the tendency of the phase to interact with dipolar/polarizable solutes.

The a-constant denotes the hydrogen-bond basicity of the system (acidic solutes will interact with a basic membrane).

The b-constant is a measure of the hydrogen-bond acidity of the system (basic solutes will interact with an acidic membrane).

The v-constant is a measure of the endoergic cavity term of the system excluding any form of intermolecular interactions.

The l-constant is a combination of exoergic dispersion forces that make a positive contribution to the l-coefficient. It mainly measures the hydrophobicity of the system.

Aspects of the above-listed molecular descriptors have been studied for three decades for solvent and solute properties, and appear to be the most general set of parameters currently available, as well as the set that would offer the best extrapolations to other work in the art. An advantage of describing skin permeability relationships using such descriptors is that information is also gained on the mechanism of permeation. In the skin chemical mixture experiments conducted in the art to date, dermal absorption is empirically assessed as epidermal permeability (steady state parameter) or flux through skin (e.g. % of applied dose absorbed; not at steady state), and not stated in terms of parameters that can be extrapolated to other penetrants based on basic molecular properties. It is thus an aspect of the present invention to provide mixture interaction studies using the framework of linear solvation energy relationships to determine which types of solution and partitioning interactions significantly alter dermal absorption. Designing chemical mixture interaction studies using this framework allows for determination of the types of chemicals expected to be susceptible to the significant interactions detected.

These molecular descriptors are also used for linking to an IPPSF model (e.g. reference molecular descriptors), and are generally applicable for other purposes (e.g. GI absorption, systemic distribution phenomenon). To use the MCF technique to determine the intermolecular descriptors [R,π,α,β,V,L], compounds of known descriptor values (e.g. reference molecular descriptors) (Abraham et al., 1991) are used to calibrate the MCF/solvent system. A full description of the experimental approach is presented in the Examples below.

IV. Isolated Perfused Porcine Skin Flap System

The isolated perfused porcine skin flap (IPPSF) system is a single-pedicle, axial pattern tubed skin flap obtained from the abdomen of female weanling Yorkshire pigs (Sus scrofa).

Figure 8:
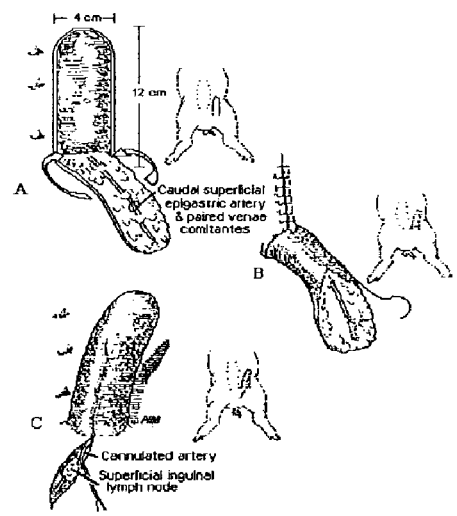
FIG. 8 is a schematic of the IPPSF surgery protocol.
Figure 9:
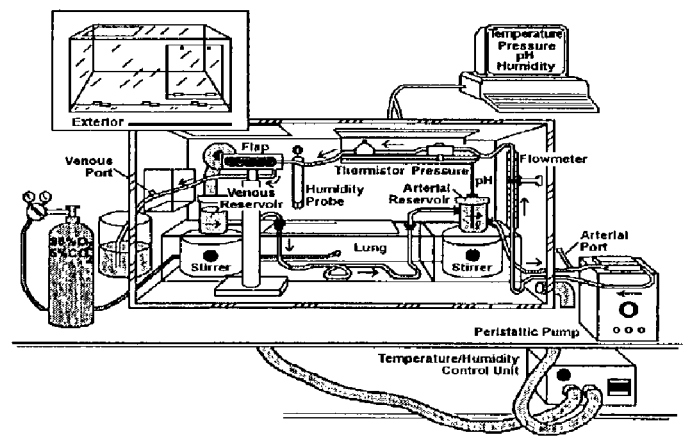
FIG. 9 is a schematic of the IPPSF perfusion chamber.

Two flaps per animal, each lateral to the ventral midline, are created in a single surgical procedure. As depicted in FIG. 8, the procedure involves surgical creation of the flap (measuring 4 cm×12 cm) perfused primarily by the caudal superficial epigastric artery and its associated paired venae comitantes (Step A & B), followed by arterial cannulation and harvest in 48 hours (Step C) (Bowman et al., 1991). The IPPSF is then transferred to a perfusion apparatus that is a custom designed temperature and humidity regulated chamber (FIG. 9). The media comprises a modified Krebbs Ringer buffer with bovine serum albumin. Normal perfusate flow is maintained at 1 ml/min/flap (3-7 ml/min/100 g) with a mean arterial pressure ranging from 30-70 mm Hg, targets consistent with in vivo values reported in the art. Viability for up to 24 hours has been confirmed through biochemical studies and extensive light and transmission electron microscopy studies (Monteiro-Riviere et al., 1987).

Compounds can be topically applied neat or diluted in vehicle under ambient (non-occluded) or occluded conditions. A relatively large dosing area of up to 10 cm$^2$ is available for compound application and is an advantage of this system. This allows for drug delivery patches, iontophoretic devices, and an applied surface area large enough to be comparable to human application. These techniques are fully described in the art (e.g. Riviere at al., 1986; Riviere and Monteiro-Riviere, 1991; Monteiro-Riviere, 1990).

Figure 10:
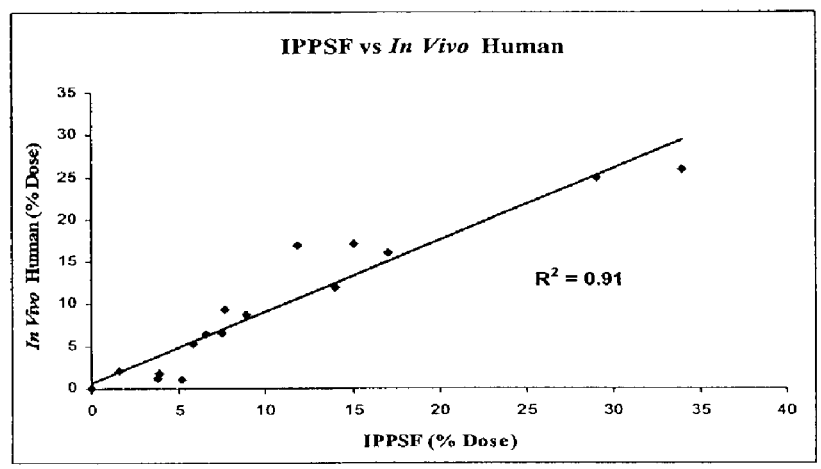
FIG. 10 is a plot of IPPSF correlation to Human In Vivo Absorption

IPPSF venous efflux profiles have been analyzed using a number of pharmacokinetic models (Williams et al., 1990; Williams and Riviere, 1995). These models integrate basic Fickian diffusion parameters to pharmacokinetic parameters based on defining differential equations. IPPSFs are the most complex model employed in these studies since it has been shown to be predictive of in vivo human absorption under a variety of exposure scenarios (Riviere et al., 1992, 1995, 2002, 2003; Wester et al., 1998). These data are plotted in FIG. 10 for 16 compounds where comparable experimental conditions (dose/unit area; vehicle) for both data sets were available. This model is able to quantitatively rank "low" versus "high" absorption compounds ($R^2$=0.91), and assess those factors that significantly modulate in vivo absorption by a wide range of physical-chemical and biological mechanisms.

estimated rate constants. This simplified model was constructed using dominant Eigen values from the more complex model to define rate-limiting processes. It describes IPPSF flux profiles under a number of different conditions (Riviere et al., 2001a, Smith et al., 1996).

Figure 11:
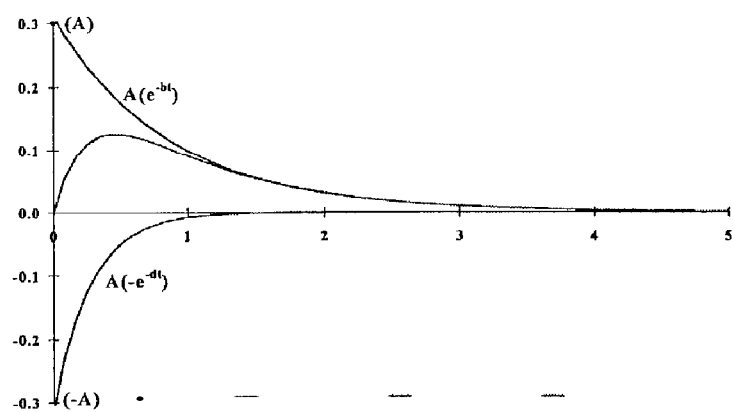
FIG. 11 is a plot of an IPPSF Pharmacokinetic Model.

The model applied to an IPPSF perfusate flux profile is depicted in FIG. 11, where the x-axis is time and the y-axis is flux into perfusate. Previously published IPPSF absorption data for nine chemicals (carbaryl, dimethylamine, methyl salicylate, paranitrophenol, pentachlorophenol, phenol, salicylic acid, sulfur mustard, and theophylline) with dose (40 µg/cm$^2$) and vehicle controlled were fit to this model (WIN-NONMIX®—Pharsight Corporation, Cary, N. C., United States of America). These compounds had molecular weights ranging from 94 to 390 and log $K_{ow}$ from −0.7 to 9.2. Using multiple regression analysis (SAS, Cary, N. C., United States of America), the resulting parameters were stepwise correlated to a large number of physical chemical parameters.

Parameters selected were similar to those previously used to predict permeability through in vitro stratum corneum diffusion cells (Potts and Guy, 1992, Buchwold and Bodor, 2001; Sartorelli et al., 1998). The relationships identified in these analyses are expected to be different than those reported using in vitro diffusion cells, since the IPPSF comprises different biological components in addition to stratum corneum. This model system, designed to predict in vivo absorption, also use plasma surrogates as perfusate since oncotic pressure is required to maintain capillary perfusion. Although this could partially confound QSAR studies linked to permeability alone, it is more reflective of the in vivo endpoint being modeled. In the IPPSF approach, the model parameters are not steady-state permeability constants but rather pharmacokinetic descriptors (rate and extent) describing a perfusate concentration-flux profile as a function of dose.

Figure 12:
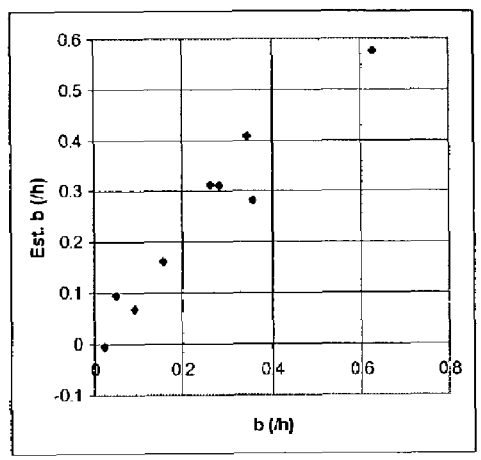
FIG. 12 is a plot of physical chemical descriptors versus IPPSF for pharmacokinetic parameter "b".
Figure 13:
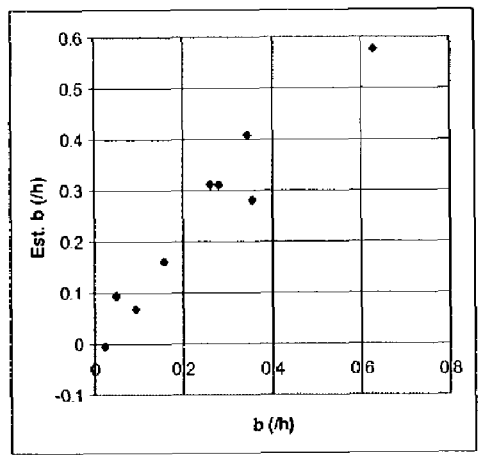
FIG. 13 is a plot of physical chemical descriptors versus IPPSF for pharmacokinetic parameter "d".

The results of this analysis identified the following significant parameters: McGowan molecular volumes ($V_m$), hydrogen bonding energies (donor H acidity and acceptor H basicity), water solubility, and s-polarizability. The correlation plots for the b and d parameters are depicted in FIGS. 12 and 13.

TABLE I

IPPSF Absorption Parameters vs. Constants - Full Model

|   | Intercept | H-acidity | H-basicity | Vm | S-Polarizability | H$_2$O Solubility | R$^2$ |
|---|---|---|---|---|---|---|---|
| A (% D/h) | 1.00522 | −0.60136 | −2.59481 | −2.04362 | 2.57048 | 0.00765 | 0.9164 |
| b (/h) | 0.91228 | −0.8142 | −0.91053 | −0.33453 | 0.33704 | 0.00331 | 0.9352 |
| d (/h) | 16.70476 | −19.34336 | −15.87366 | −1.48847 | 2.31685 | 0.06775 | 0.9503 |

Pharmacokinetic modeling allows integration of relevant physical chemical parameters into a model predictive of IPPSF (and by extension in vivo human) absorption. It is based on defining IPPSF absorption profiles using the simplest pharmacokinetic model that reflects rate-limiting processes involved in absorption without relying on complex mathematically non-identifiable compartmental models previously used (Williams et al., 1996). This simplified model describing flux (Y(t)) at time t is:

$$Y(t)(\mu g/min) = A(e^{-bt} - e^{-dt}) \quad \text{(Eq. 5)}$$

where A is the intercept term of the flux-time profile reflecting dose and extent of compound absorption and b and d are the These data clearly demonstrate that IPPSF flux profiles can be characterized by five physical chemical parameters: H acidity, H basicity, $V_m$, S-Polarizability and H$_2$O solubility. The correlation of the area under the curve (AUC) of the IPPSF flux profile to these parameters was very high ($R^2$=0.978), an important finding since AUC from skin can be a prime measure of systemic exposure in a toxicological risk assessment and can serve as the input function for a physiologically-based pharmacokinetic model for a compound (Dixet et al., 2003).

Analysis of existing IPPSF perfusate flux profiles strongly correlating [A, b, d] to [H acidity, H basicity, $V_m$, S-Polarizability and H$_2$O solubility] supports the further correlation of

[a, b, d] to the new set of molecular descriptors [R, π, α, β, V and L] that contain similar physical chemical information but are more general descriptors and amenable to the MCF approach employed in one embodiment of the present invention. Moreover, the existing correlation of IPPSF profiles to in vivo human absorption increases the reliability of these data to be applied to relevant risk assessments in another embodiment of the present invention.

IV. MCF Apparatus and Method

Referring now to the drawings, FIG. 3 shows an embodiment of a simulated biological membrane (e.g. a skin-imitating membrane) coated fiber (MCF). A piercing needle 4 is attached to a needle base 3. A sealing septum 2 is inserted in the needle base 3b. The needle base has a taper end 3c for positioning during absorption. Fiber attachment tubing 5 can slide inside of the piercing needle through the sealing septum. The top end of the fiber attachment tubing is attached to a holding tip 1. A chemically inert fiber 6 is attached to the lower end of the fiber attachment tubing. One section of the inert fiber is coated with a membrane 7.

This simulated biological membrane is used to partition compounds from solutions, and desorb the partitioned compounds into the injector of a gas chromatograph (GC) or a high performance liquid chromatograph (HPLC) while keeping the membrane unchanged. In one embodiment the membrane has characteristics that cover a wide-strength range of molecular interactions. Indeed in one embodiment, as large a range as possible is provided. Optionally, the membrane can simulate a biological membrane (as defined herein) of interest. For example, a skin-imitating membrane preferably has similar absorption properties as skin. Additionally, the membrane preferably has high thermal stability for desorption of the compounds into the GC injector without damage to the membrane itself; or have high solvent stability to desorb the compounds into the HPLC column without damage to the membrane itself. Several materials can be used for this purpose, including but not limited to: polydimethylsiloxane (PDMS), polyacrylate, crosslinked PDMS, polydimethylsiloxane-polycarbonate block copolymer, and other stationary phases used in GC columns and HPLC columns that provide similar absorption properties as skin. Additional representative materials are disclosed in the Examples and indeed, in one embodiment of the present invention, the use of multiple materials, alone and in combination, is provided.

The exposing surface area (A) of the skin-imitating membrane is determined by the membrane coating radius ($R_m$) and the coating height (H). The volume $V_m$ of the skin-imitating membrane is determined by the membrane thickness ($\delta_m$), the coating radius ($R_m$) and the coating height (H). The volume ($V_d$) is the volume of the donor solution. When the skin-imitating membrane coated fiber not in use, the fiber is extracted into the inside of the piercing needle to protect the membrane from damaging. To do the absorption experiment, the membrane-coated fiber 7 is pressed out of the piercing needle 4 by pressing the holding tip 1 while holding the needle base 3. The membrane-coated fiber is exposed into the donor solution and fixed in position by the taper end of the needle base.

The holding tip 1 and the needle base 3 are made of plastic material. The piercing needle 4 and the fiber attachment tubing 5 are made of stainless steel. The inside of the fiber attachment tubing 5 is filled with reinforcing material to increase its mechanical strength. The inert fiber 6 is a fused-silica fiber or a stainless steel fiber, or other suitable inert fiber as would be apparent to one of ordinary skill in the art after a review of the disclosure of the present invention set forth herein.

FIG. 4 shows the design of the absorption container with a special needle holding cap and water jacket. The needle holding cap 10 has several holes drilled in a specific shape 12 to fit the taper end of the needle base 3. The number of holes is determined by the number of needle to be used, for instance, 4, 6, 8 or more. All of the holes 12 are on the same radius $R_c$, which is the radius of the membrane coated fiber to the vertical centerline of the container.

The needle holding cap 10 is well fit into the solution container 20 for precise control of the radius $R_c$. The membrane-coated fiber is immersed in the donor solution 26 for partitioning the compounds from the solution. The temperature of the solution is maintained by the water jacket 22 with inlet 25 and outlet 24. The needle holding cap 10 is made of plastic materials by molding or machine. The absorption container 20 is preferably made of glass or TEFLON® PTFE to reduce its chemical absorption.

FIG. 5 shows the experiment setup for percutaneous absorption study with the membrane-coated fiber. The absorption container 20 sits on a magnetic stirrer 30. A magnetic stir bar 21 is stirring the solution 26 in the absorption container. The stirring rate is controlled by a rate controller 34 and displayed on a tachometer 32. Needle holding cap 10 positions the membrane-coated fibers 3. Thus, all of the geometric parameters, such as, $R_c$, membrane coating radius R, membrane thickness $\delta_m$ are preferably kept constant (i.e. uniform) with the present setup. The water jacket maintains the solution at constant temperature.

Figure 15:
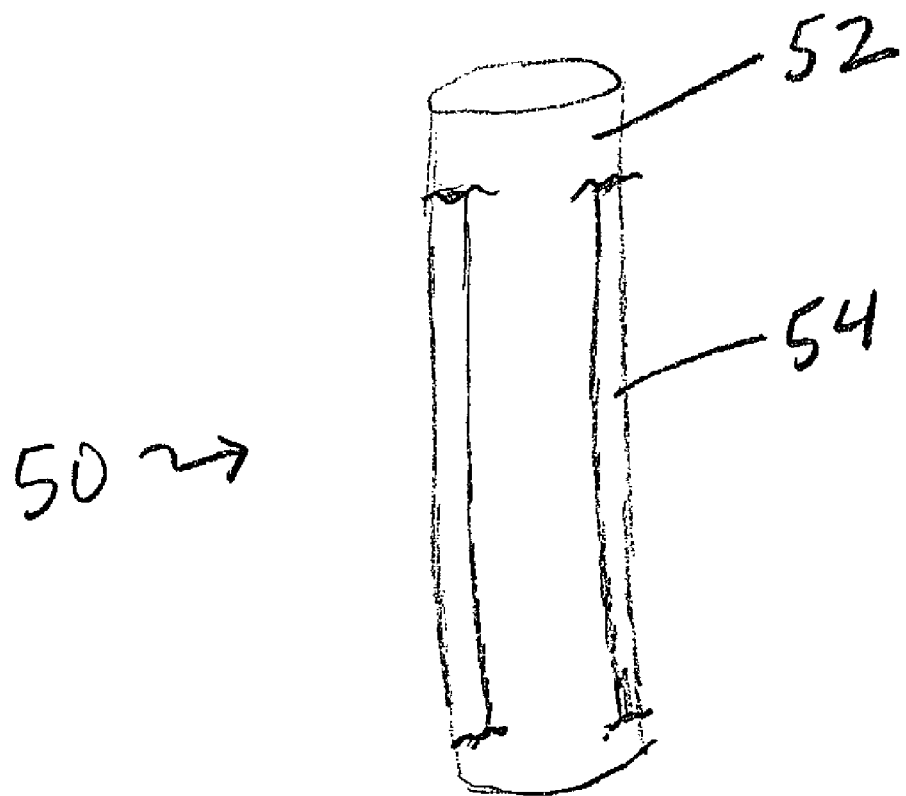
FIG. 15 is a schematic perspective view of one embodiment 50 of a membrane assembly.

Referring to FIG. 15, shown is another embodiment of a membrane assembly, which is designated as 50. Membrane assembly 50 comprises a membrane 52 mounted inside tube 54. One, two, or indeed any desired number of membranes 52 can be mounted inside tube 54, as is feasible based on the dimensions of membrane 52 and tube 54. Membranes 52 can be the same or different. Tube 54 can comprise a stainless needle (e.g. stainless steel), capillary tube, cylinder, or another suitable structure as would be apparent to one of ordinary skill in the art after a review of the present disclosure. Additionally, tube 52 can have any suitable cross-sectional configuration, such as but not limited to one of circular, triangular, and rectangular (including a square). Assembly 50 allows compounds to partition into membrane 52 inside tube 54 and to desorb into the GC injector for quantitative analysis.

In one embodiment, the present invention can be implemented in hardware, firmware, software, or any combination thereof. In one exemplary embodiment, the methods and data structures for determining a molecular descriptor of absorption for a candidate compound and/or for assessing susceptibility of a candidate compound to absorption into a biological membrane can be implemented as computer readable instructions and data structures embodied in a computer-readable medium. The data structures can comprise one or more data fields (e.g. 2,3,4,5 or more such data fields) containing molecular descriptors of different types and values, e.g. reference molecular descriptors. Computer readable instructions for implementing Equations 7, 8, and 10 are also provided.

Figure 14:
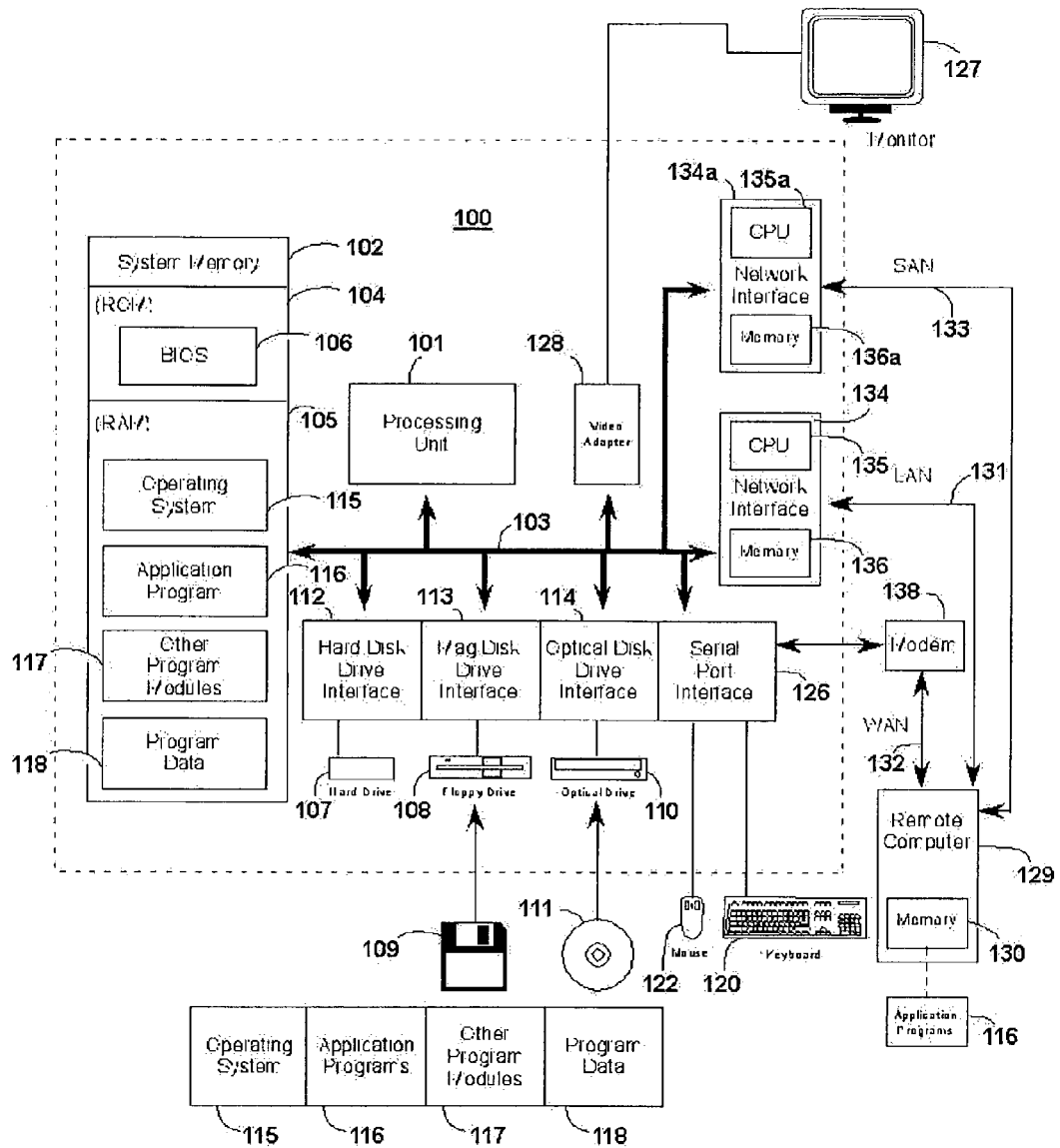
FIG. 14 illustrates an exemplary general purpose computing platform 100 upon which the methods and systems of the present invention can be implemented.

With reference to FIG. 14, an exemplary system for implementing the invention includes a general purpose computing device in the form of a conventional personal computer 100, including a processing unit 101, a system memory 102, and a system bus 103 that couples various system components including the system memory to the processing unit 101. System bus 103 can be any of several types of bus structures including a memory bus or memory controller, a peripheral bus, and a local bus using any of a variety of bus architectures. The system memory includes read only memory (ROM) 104 and random access memory (RAM) 105. A basic input/output system (BIOS) 106, containing the basic routines that help to transfer information between elements within personal computer 100, such as during start-up, is stored in ROM 104. Personal computer 100 further includes a hard disk drive 107 for reading from and writing to a hard disk (not shown), a magnetic disk drive 108 for reading from or writing to a removable magnetic disk 109, and an optical disk drive 110 for reading from or writing to a removable optical disk 111 such as a CD ROM or other optical media.

Hard disk drive 107, magnetic disk drive 108, and optical disk drive 110 are connected to system bus 103 by a hard disk drive interface 112, a magnetic disk drive interface 113, and an optical disk drive interface 114, respectively. The drives and their associated computer-readable media provide non-volatile storage of computer readable instructions, data structures, program modules, and other data for personal computer 100. Although the exemplary environment described herein employs a hard disk, a removable magnetic disk 109, and a removable optical disk 111, it will be appreciated by those skilled in the art that other types of computer readable media which can store data that is accessible by a computer, such as magnetic cassettes, flash memory cards, digital video disks, Bernoulli cartridges, random access memories, read only memories, and the like may also be used in the exemplary operating environment.

A number of program modules can be stored on the hard disk, magnetic disk 109, optical disk 111, ROM 104, or RAM 105, including an operating system 115, one or more applications programs 116, other program modules 117, and program data 118. System memory 104 and/or 105 can also include a search engine, a database manager, and a comparator program having instructions for implementing the search, management, compilation (e.g. addition and deletion of molecular descriptors from database or other aspects of memory), comparing data, assessing data, and displaying the molecular descriptors of absorption for a candidate compound and comparisons thereof. In one embodiment, search engine and database manager can include a software database application such as FILEMAKER 5.5v2 UNLIMITED produced by FileMaker, Inc. of Santa Clara, Calif., United States of America. Other software programs and packages are disclosed in the Examples.

A user can enter commands and information into personal computer 100 through input devices such as a keyboard 120 and a pointing device 122. Other input devices (not shown) can include a gas chromatograph, a high performance liquid chromatography apparatus, a microphone, touch panel, joystick, game pad, satellite dish, scanner, or the like. These and other input devices are often connected to processing unit 101 through a serial port interface 126 that is coupled to the system bus, but can be connected by other interfaces, such as a parallel port, game port or a universal serial bus (USB). A monitor 127 or other type of display device is also connected to system bus 103 via an interface, such as a video adapter 128. In addition to the monitor, personal computers typically include other peripheral output devices, not shown, such as speakers and printers. With regard to the present invention, the user can use one of the input devices to input data indicating the user's preference between alternatives presented to the user via monitor 127.

Personal computer 100 can operate in a networked environment using logical connections to one or more remote computers, such as a remote computer 129. Remote computer 129 can be another personal computer, a server, a router, a network PC, a peer device or other common network node, and typically includes many or all of the elements described above relative to personal computer 100, although only a memory storage device 130 has been illustrated in FIG. 14. The logical connections depicted in FIG. 14 include a local area network (LAN) 131, a wide area network (WAN) 132, and a system area network (SAN) 133. Local- and wide-area networking environments are commonplace in offices, enterprise-wide computer networks, intranets and the Internet.

System area networking environments are used to interconnect nodes within a distributed computing system, such as a cluster. For example, in the illustrated embodiment, personal computer 100 can comprise a first node in a cluster and remote computer 129 can comprise a second node in the cluster. In such an environment, it is preferable that personal computer 100 and remote computer 129 be under a common administrative domain. Thus, although computer 129 is labeled "remote", computer 129 can be in close physical proximity to personal computer 100.

When used in a LAN or SAN networking environment, personal computer 100 is connected to local network 131 or system network 133 through network interface adapters 134 and 134a. Network interface adapters 134 and 134a can include processing units 135 and 135a and one or more memory units 136 and 136a.

When used in a WAN networking environment, personal computer 100 typically includes a modem 138 or other device for establishing communications over WAN 132. Modem 138, which can be internal or external, is connected to system bus 103 via serial port interface 126. In a networked environment, program modules depicted relative to personal computer 100, or portions thereof, can be stored in the remote memory storage device. It will be appreciated that the network connections shown are exemplary and other approaches to establishing a communications link between the computers can be used.

While in one embodiment the present invention pertains to percutaneous absorption, it is further provided that other biological barriers and membranes can be analyzed. Representative barriers and/or membranes include but are not limited to subcellular, cellular, oral/mucosal, gastrointestinal, blood-brain, respiratory-lung, nasal, ocular and subconjuctival. Thus, as used herein and in the claims, the term "simulated biological membrane" is meant to encompass other biological barriers and membranes, including but not limited to those listed above, as well as the skin-imitating membrane disclosed above. The materials disclosed above and in the Examples that can be used alone or in combination to prepare the skin-imitating embodiment of a membrane of the present invention can also be used alone or in combination to prepare a simulated biological membrane of the present invention. In one embodiment the membrane has characteristics that cover a wide-strength range of molecular interactions. Indeed in one embodiment, as large a range as possible is provided.

It must be noted that as used herein and in the appended claims, the singular forms "a", "an", and "the" include plural referents unless the context clearly dictates otherwise.

V. MCF Equations

Figure 2:
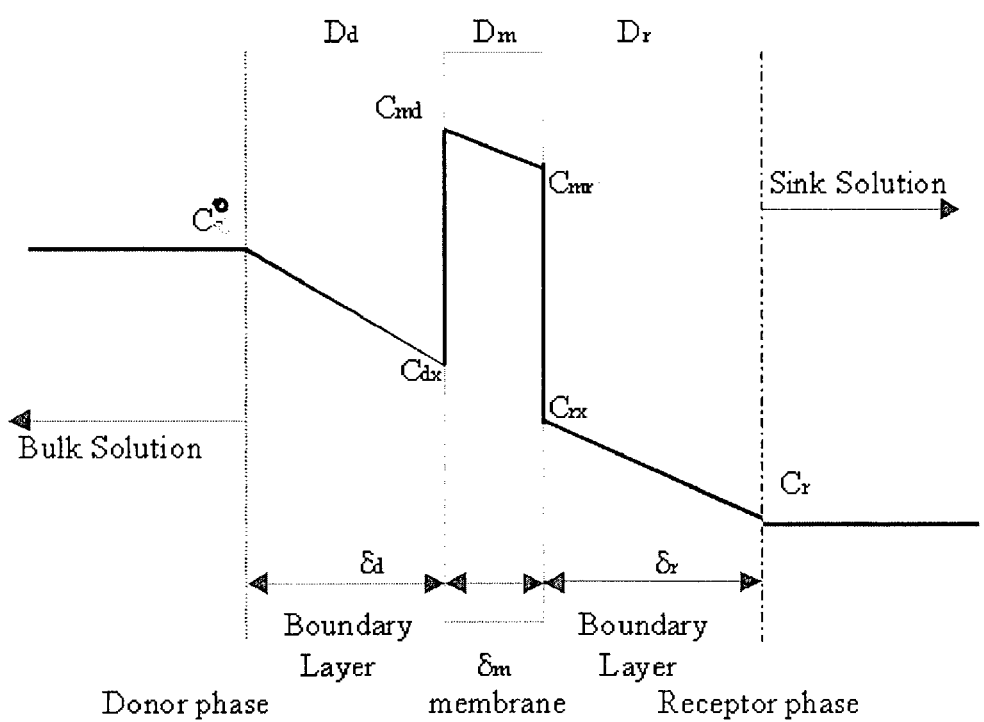
FIG. 2 is a schematic depicting basic compartments of a diffusion cell used in percutaneous absorption. $C^\circ$: bulk concentration in the donor phase; $C_{dx}$: surface concentration in the donor phase; $C_{md}$: surface concentration in the membrane contacting the donor phase; $C_{mr}$: surface concentration in the membrane contacting the receptor phase; $C_{rx}$: surface concentration in the receptor phase; $C_r$: bulk concentration in the receptor phase; $\delta_d$: thickness of the boundary layer of the donor phase; $\delta_r$: thickness of the boundary layer of the receptor phase; $\delta_m$: Thickness of the membrane. $D_d$, $D_m$, and $D_r$ are the diffusion coefficients in the donor phase, in the membrane, and in the receptor phase, respectively.

The absorption mechanism in a conventional diffusion cell is shown in FIG. 2. This complicated absorption mechanism can be separated into two sections, permeation section and penetration section. The permeation section comprises the donor phase, the boundary layer ($\delta_d$), and the membrane; the penetration section comprises the membrane, the boundary layer ($\delta_r$), and the receptor phase. When a membrane-coated fiber is used to study the absorption mechanism in accordance with the present invention, only one section is involved. In the following theoretical derivation only the permeation section will be considered.

If diffusion is the rate-controlling factor, Fick's first law of diffusion can be expressed as follows for a continuous flowing system at the boundary region between the donor phase and the skin-imitating membrane:

$$F = -D_d A \frac{dC_d}{dx} = -D_m A \frac{dC_m}{dx}, \quad \text{(MCF-1)}$$

where F is the diffusion flux of a given permeant from the donor phase to the membrane surface, which is equal to the diffusion flux of the permeant from the membrane surface into its inner membrane phase for a balanced mass transfer; A is surface area of the silastic membrane; $D_d$ is the diffusion coefficient of the permeant in the donor phase; $D_m$ is the diffusion coefficient of the permeant in the membrane phase; $C_d$ and $C_m$ are concentrations of the permeant in donor phase and in membrane phase, respectively; and x is an axial perpendicular to the membrane surface. The diffusion flux can also be expressed in permeation time as follows:

$$F = \frac{dn}{dt}, \quad \text{(MCF-2)}$$

where n is the amount of the permeant in the membrane. Then Eq. MCF-1 becomes:

$$\frac{\partial n}{\partial t} = -D_d A \frac{\partial C_d}{\partial x} = -D_m A \frac{\partial C_m}{\partial x}. \quad \text{(MCF-3)}$$

If the experimental hydrodynamic condition is well defined, for example, stirring at constant speed, a steady-state diffusion can be established, at which the thickness of the boundary layer is assumed to be constant. Since the silastic membrane coated on the fiber is a thin film, the diffusion layer is the entire thickness of the membrane and the diffusion is in steady-state. Thus, the partial differential equation (Eq. MCF-3) can be simplified to a normal differential equation:

$$\frac{dn}{dt} = D_d A \frac{C_d - C_{dx}}{\delta_d} = D_m A \frac{C_{md} - C_{mr}}{\delta_m}, \quad \text{(MCF-4)}$$

where $C_d$ is the concentration of the permeant in the bulk donor phase. For infinite dose it is the original concentration $C^\circ$. $C_{dx}$ is the surface concentration of the permeant in the donor phase, which is the driving force for the permeant diffused into the membrane. $\delta_d$ is the thickness of the donor boundary layer, $C_{md}$ is the concentration of the permeant in the membrane surface, $C_{mr}$ is the concentration of the permeant in the membrane contacting the fused silica fiber, and $\delta_m$ is the thickness of the skin-imitating membrane as shown in FIG. 3.

At the membrane surface, the concentration $C_{dx}$ in the donor phase and the concentration $C_{md}$ in the membrane phase are governed by the partition equilibrium. If the partition equilibrium can be quickly established, the partition coefficient is expressed as follows:

$$K = \frac{C_{md}}{C_{dx}} \quad \text{or} \quad C_{dx} = \frac{C_{md}}{K} \quad \text{(MCF-5)}$$

and, in the bulk solution of the donor phase, we have $$C_d = C^\circ - \frac{n}{V_d}. \quad \text{(MCF-6)}$$

Substituting Eq. MCF-5 and Eq. MCF-6 into Eq. MCF-4, we have $$\frac{D_d}{\delta_d}\left(C^\circ - \frac{n}{V_d} - \frac{C_{md}}{K}\right) = \frac{D_m}{\delta_m}(C_{md} - C_{mr}). \quad \text{(MCF-7)}$$

As assumed above the silastic membrane is a thin uniform film and in steady state diffusion, the concentration gradient of the permeant can be approximated to be linear in the membrane phase. Then, the permeation amount can be approximated by the mean concentration increase as follows:

$$n = V_m \frac{C_{md} + C_{mr}}{2}. \quad \text{(MCF-8)}$$

Solving Eq. MCF-7 and Eq. MCF-8 for $C_{md}$ and $C_{mr}$, we have $$C_{md} - C_{mr} = \frac{2KD_d\delta_m C^\circ}{D_d\delta_m + 2KD_m\delta_d} - \quad \text{(MCF-9)}$$
$$\frac{2D_d\delta_m(KV_m + V_d)}{V_d V_m(D_d\delta_m + 2KD_m\delta_d)}n.$$

Substituting Eq. MCF-9 into Eq. MCF-4, we have $$\frac{dn}{dt} = \frac{D_m}{\delta_m} A(C_{md} - C_{mr}) \quad \text{(MCF-10)}$$
$$= \frac{2AKD_d D_m C^\circ}{D_d\delta_m + 2KD_m\delta_d} - \frac{2AD_d D_m(KV_m + V_d)}{V_d V_m(D_d\delta_m + 2KD_m\delta_d)}n$$

Let, $$a = \frac{2AD_d D_m(KV_m + V_d)}{V_d V_m(D_d\delta_m + 2KD_m\delta_d)} \quad \text{(MCF-11)}$$

$$b = \frac{2AKD_d D_m C^\circ}{D_d\delta_m + 2KD_m\delta_d}$$

The differential equation (Eq. 1 MCF-0) can be simplified as:

$$\frac{dn}{dt} = b - an \quad \text{(MCF-12)}$$

Solving Eq. MCF-12 with the initial conditions, when t=0, n=0, we have $$n = [1 - \exp(-at)]\frac{b}{a} \quad \text{(MCF-13)}$$

Putting the a and b expressions (Eq. MCF-11) back into Eq. MCF-13, we have $$n = [1 - \exp(-at)]\frac{KV_d V_m C°}{KV_m + V_d} \quad \text{(MCF-14)}$$

When permeation equilibrium is reached at long enough of time, t→∞, the maximum equilibrium amount n° can be obtained from Eq. 1 MCF-4 as follows:

$$n° = \frac{KV_d V_m C°}{KV_m + V_d} \quad \text{(MCF-15)}$$

$$\text{or, } K = \frac{n° V_d}{V_m(V_d C° - n°)} \quad \text{(MCF-15a)}$$

Thus, equation MCF-14 becomes $$n = [1 - \exp(-at)] n° \quad \text{(MCF-16)}$$

By rearranging the expression of constant a (Eq. MFC-11), the contributions from the membrane and the boundary layer are evident:

$$a = \frac{2A(K/V_d + 1/V_m)}{\delta_m/D_m + 2K\delta_d/D_d} \quad \text{(MFC-17)}$$

In the denominator, the first item ($\delta_m/D_m$) is the contribution of the membrane while the second item ($2K \delta_d/D_d$) is the contribution of the boundary layer. When the partition coefficient (K) is large enough to satisfy a condition, $\delta_m/D_m << 2K \delta_d/D_d$, the contribution of the membrane can be neglected:

$$a = \frac{AD_d(K/V_d + 1/V_m)}{K\delta_d} \quad \text{(MFC-18)}$$

$$\text{or, } \delta_d = \frac{AD_d(K/V_d + 1/V_m)}{aK} \quad \text{(MFC-18a)}$$

The diffusion coefficient in the membrane ($D_m$) can be calculated from the measured parameters by rearranging Eq. MFC-11:

$$D_m = \frac{a\delta_m}{2A(K/V_d + 1/V_m) - 2aK\delta_d/D_d} \quad \text{(MFC-19)}$$

Once the partition coefficient (K), the diffusion coefficient ($D_m$) and the thickness of the membrane ($\delta_m$) are known, permeation coefficient ($k_p$) can be calculated from its definition:

$$k_p = \frac{KD_m}{\delta_m} \quad \text{(MFC-20)}$$

LABORATORY EXAMPLES

The following Laboratory Examples have been included to illustrate preferred modes of the invention. Certain aspects of the following Laboratory Examples are described in terms of techniques and procedures found or contemplated by the present co-inventors to work well in the practice of the invention. These Laboratory Examples are exemplified through the use of standard laboratory practices of the co-inventors. In light of the present disclosure and the general level of skill in the art, those of skill will appreciate that the following Laboratory Examples are intended to be exemplary only and that numerous changes, modifications and alterations can be employed without departing from the spirit and scope of the invention.

Laboratory Example 1

Polydimethylsiloxane (PDMS) Membrane Coated Fiber

Figure 6:
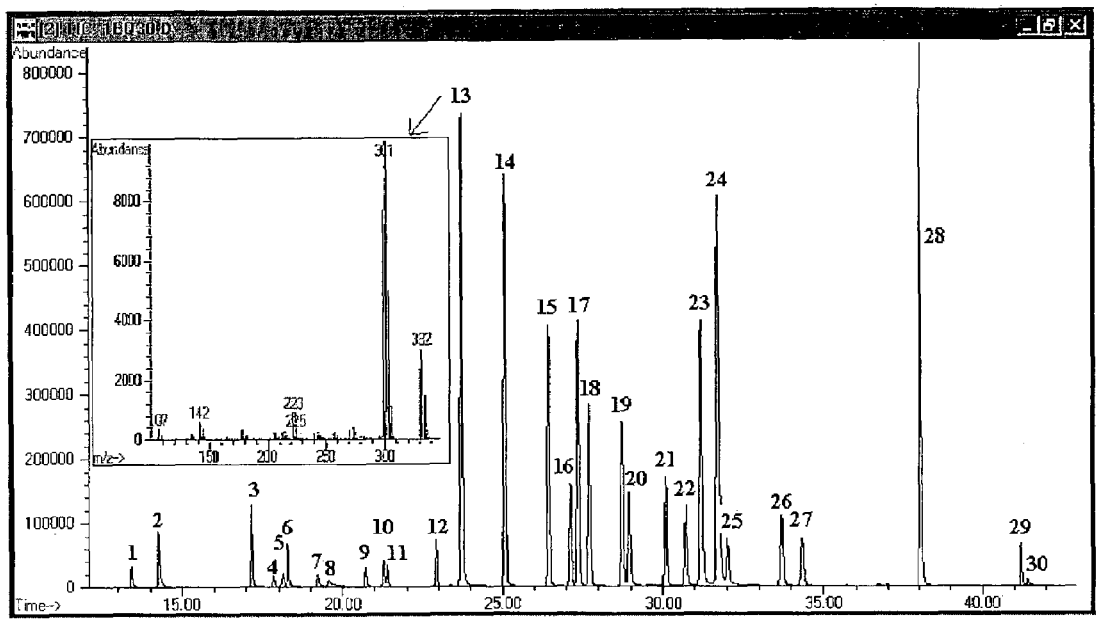
FIG. 6 shows GC/MS spectra acquired with a HP 5890 gas chromatograph coupled with a HP 5970B mass selective detector and a polydimethylsiloxane (PDMS) membrane coated fiber partitioned for 30 minutes in a solution containing 30 compounds. The 30 compounds were: 1: Terrazole, 2: Chloroneb, 3: a-BHC, 4: Simazine, 5: Atrazine, 6: b-BHC, 7: g-BHC, 8: d-BHC, 9: Chlorothalonil, 10: Heptachlor, 11: Alachlor, 12: Aldrin, 13: Dacthal, 14: Heptachlor epoxide, 15: tr-Chlordane, 16: Endosulfan I, 17: cis-Chlordane, 18: tr-Nonachlor, 19: Dieldrin, 20: p,p-DDE, 21: Endrin, 22: Endosulfan II, 23: Chlorobenzilate, 24: p,p-DDD, 25: Endrin aldehyde, 26: Endosulfan sulfate, 27: p,p-DDT, 28: Methoxychlor, 29: cis-Permethrin and 30: tr-Permethrin.

FIG. 6 shows a GC/MS spectra acquired with a HP 5890 gas chromatograph coupled with a HP 5970B mass selective detector and a polydimethylsiloxane (PDMS) membrane coated fiber (MCF) partitioned for 30 minutes in a solution containing 30 compounds. The injection port was maintained at 280° C. for sample vaporization and thermal desorption.

Separation was performed on a 30 m×0.25 mm (i.d.)×0.25 μm (df) Rtx-5MS capillary column (Restek Corp., Bellefonte, Pa., United States of America). The transfer line temperature was set at 250° C. The column oven was programmed as follows: held at the initial temperature 100° C. for 1 min., ramped at 15° C./min to 150° C., 1° C./min to 220° C. and 3° C./min. to 280° C., and held for 5 min. An electronic pressure control was used to maintain a carrier gas flow of 1.00 mL/min helium.

The membrane-coated fiber was conditioned in flowing helium at 280° C. for 10 min. The absorption experiments were performed as follows. The membrane-coated fiber was positioned in the absorption container and the membrane section was immersed into the solution to be studied. The solution was a standard mixture containing 30 components having a wide range of octanol-water partition coefficients. The concentration of each compound in the solution is 8 ng/mL. The solution was stirred at 400 rpm. After the membrane-coated fiber was immersed in the solution for a given time, the membrane-coated fiber was transferred directly into the injection port of the gas-chromatograph for quantitative analysis.

It was shown that a complex mixture containing 30 compounds can be studied at a single run. Each compound in the complex mixture was identified by its MS fingerprint spectra.

The absorption amount of each compound is obtained by its peak area in the spectra against its calibration standard. See FIG. 6.

Laboratory Example 2

Figure 7:
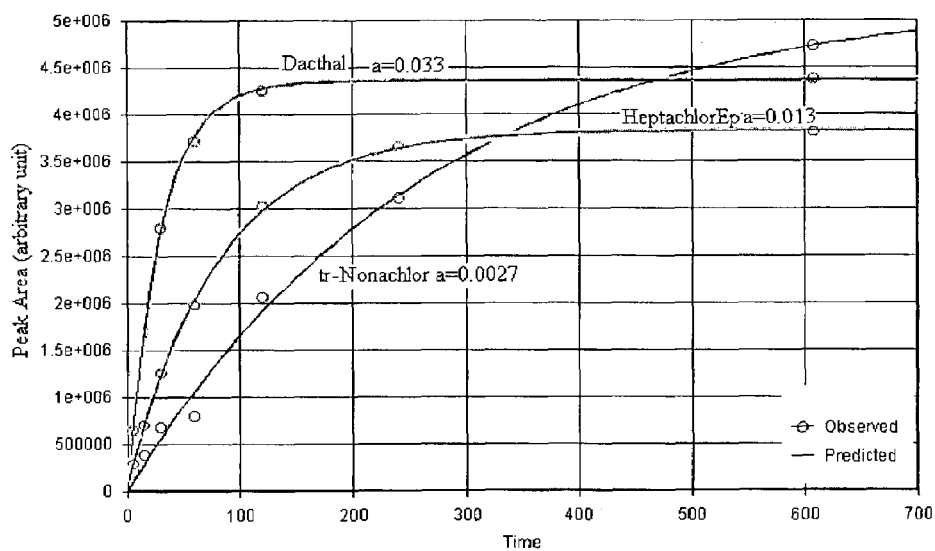
FIG. 7 shows the absorption amount versus time profiles for three compounds, Dacthal, Heptachlor Epoxide and tr-Nonachlor, and their regressions.

Screening of Three Candidate Compounds Using Polydimethylsiloxane (PDMS) Membrane Coated Fiber FIG. 7 shows the absorption amount versus time profiles for three compounds, Dacthal, Heptachlor Epoxide and tr-Nonachlor. The experimental procedures are same as in FIG. 6. The absorption time was set as 5, 15, 30, 60, 120, 240, and 635 min. In one set of experiments, the absorption amount versus time profiles were produced for each compounds in the solution.

When permeation equilibrium is reached, the concentration gradients in the boundary layer and in the membrane will be vanished. The equilibrium concentration $$\left(C_m^e = \frac{n^\circ}{V_m}\right)$$

in the membrane and the equilibrium concentration left in the donor phase $$\left(C_d^e = C^\circ \frac{n^\circ}{V_d}\right)$$

is governed by the partition equilibrium:

$$K = \frac{C_m^e}{C_d^e} = \frac{n^\circ V_d}{V_m(V_d C^\circ - n^\circ)} \quad \text{(MCF-21)}$$

It is seen that Eq. MCF-21 is exactly the same form as Eq. MCF-15a derived from the proposed theoretical model. This establishes that the theoretical derivation and assumptions made are adequate.

The partition coefficient K can be calculated from Eq. MCF-15a if the equilibrium amount ($n^\circ$) is known. With the present invention there are at least two optional methods to obtain the equilibrium permeation amount. One is to measure the permeation amount at prolonged equilibration time, at which equilibrium permeation is assumed to be reached. This is easy for small compounds with lower partition coefficients. For larger compounds with high partition coefficients equilibrium cannot be reached for days or weeks. Another method is to use the initial permeation amounts sampled in a limited period of time, and use the Eq. MCF-16 to simulate the equilibrium amount as described in the following.

The regression of Eq. MCF-16 with the permeation amount (n) versus permeation time (t), two constants, "a" and $n^\circ$, can be obtained. The constant $n^\circ$ is the maximum permeation amount at the permeation equilibrium. The constant "a" describes how fast the permeation can reach equilibrium. The larger the constant "a", the faster the permeation equilibrium can be reached.

With the present invention a complex mixture containing even 30 compounds can be studied in a single run of experiment. Representative percutaneous absorption parameters, i.e. molecular descriptors, which can be calculated for each compound, are as follows:

(a) the partition coefficient between the membrane and the solution (K) is calculated from Eq. MCF-15a when the maximum equilibrium permeation amount is obtained for each compound;

(b) The thickness of the boundary layer and the diffusion coefficients in the membrane ($D_m$) and in the donor solution ($D_d$) were obtained as follows:

The diffusion coefficient in the aqueous donor solution ($D_d$) was estimated with a published method (J. A. Schramke, S. F. Murphy, W. J. Doucette, and W. D. Hintze. Prediction of aqueous diffusion coefficients for organic compounds at 25° C. *Chemosphere* 38:2381-2406 (1999))

$$D_d = \frac{13.26 \times 10^{-5}}{\mu^{1.4} V_a^{0.589}} \quad \text{(MCF-22)}$$

where $D_d$ is the diffusion coefficient of a given compound in the donor solution (cm$^2$/s), $\mu$ is the viscosity of the aqueous solution ($\mu$=0.8937 centipoise at 25° C.), and $V_a$ is the molar volume of the compound (cm$^3$/mole). The molar volumes of the compounds were compiled from published reference database. The thickness ($\delta_m$), length (h) and volume ($V_m$) of the membrane-coated fiber were 100 μm, 1.00 cm and 0.612 μl, respectively. The surface area of the membrane (A) was calculated from the known physical parameters of the membrane ($A=V_m/\delta_m+\pi h\delta_m$).

(c) The thickness of the boundary layer ($\delta_d$) was estimated by an approaching method, i.e., $\delta_d$ value was calculated for each compound with Eq. MCF-18a from the obtained parameters (a and K) and the estimated $D_d$ value. The calculated log($\delta_d$) versus log K is plotted. When the partition coefficient (K) is high enough to satisfy the condition, $\delta_m/D_m<<2K\,\delta_d/D_d$, the thickness of the boundary layer is approached.

(d) The diffusion coefficient of a given compound in the membrane ($D_m$) was calculated from the measured parameters with Eq. MCF-19.

(e) The permeation coefficient of the membrane was calculated from its definition (Eq. MCF-20) when the partition coefficient and the diffusion coefficient and the thickness of the membrane are known.

Examples 3 and 4

Experimental Determination of Molecular Descriptors

The focus of these Examples is to adapt the general solvation equation for partition coefficients to allow for experimental determination of the molecular descriptors for any study compounds using the MCF technique in a framework coupled both to predicting percutaneous absorption in the IPPSF (which is equivalent to predicting absorption in vivo, such as in human beings) and assessing chemical mixture or solvent effects. The linear solvation energy relationship (Eq. 4) is the basis for linking these physical chemical properties of a penetrant to permeation through skin using the IPPSF model. Similar molecular descriptors appear to suitably predict disposition of a topically applied compound in the IPPSF. This approach allows the partition coefficient to be parameterized in an experimental framework amenable to the assessment of complex chemical mixture interactions using multiple MCF exposures. Thus, provided herein is an experimental system using the MCF technique that can generate molecular descriptors that are predictive of IPPSF disposition, and by extension, in vivo absorption, and that are also amenable to direct and rapid experimental determination of solvent effects, mixture effects, or formulation effects.

The basic solvation equation (Eq. 4) to be used in these Examples is repeated for convenience as:

$$\log K_{m/s} = c + rR + s\pi + a\alpha + b\beta + vV + l \log L \quad \text{(Eq. 4)}$$

The focus of these experiments is to develop an experimental approach using the MCF technique to calculate the molecular descriptors [R, $\pi$, $\alpha$, $\beta$, and L] suitable for prediction of [A, b and d] for a specific penetrant as parameterized in the IPPSF kinetic model. These parameters are experimentally determined in MCFs so that effects of solvent and chemical interactions in subsequent experiments can be quantitated based on changes in a fiber's log $K_{m/s}$ mapped onto values of the molecular descriptors that link both the MCF and IPPSF systems.

Example 3

Membrane-Coated Fiber (MCF) Technique

Log $K_{m/s}$ for a membrane-solvent system is determined experimentally by measuring the maximum equilibrium absorption amount ($n^\circ$):

$$\log K_{m/s} = \frac{C_{me}}{C_{de}} = \frac{n^\circ V_d}{V_m(V_d C^\circ - n^\circ)} \quad \text{(Eq. 6)}$$

where $C^\circ$ is the initial concentration of the given compound in the donor solution, $V_d$ is the volume of the donor solution, $V_m$ is the volume of the membrane, $C_{me}$ is the equilibrium concentration in the membrane ($C_{me} = n^\circ/V_m$) and $C_{de}$ is the equilibrium concentration in the donor solution ($C_{de} = C^\circ - n^\circ/V_d$). $C^\circ$ ranges from 1 to 100 ng/ml in these studies. Eq. 6 is similar to as Eq. MCF-21 and is renumbered here for convenience in describing Examples 3 and 4.

System parameters or strength coefficients are determined for a specific fiber to provide for the determination of molecular descriptors [R, $\pi$, $\alpha$, $\beta$, and L] for a specific solute penetrant using the MCF technique. In order to generate robust estimates of these descriptors, multiple MCFs with different physical properties and a large number of solutes with known molecular descriptors are used to assure that the estimation of the molecular descriptors is robust across compounds of diverse biophysical properties. In this calibration phase, literature values of [R, $\pi$, $\alpha$, $\beta$, V and L] are used. Thus, calibration chemicals whose descriptors can be obtained are employed. Once the MCF system is calibrated, determination of molecular descriptors [R, $\pi$, $\alpha$, $\beta$ and L] for an unknown chemical is accomplished by determining a series of log $K_{m/s}$ for the chemical with the calibrated MCFs. The intrinsic volume V does not need experimental determination as theoretically, significant mixture interactions should not be linked to this descriptor. The intrinsic volume (V) can be calculated using algorithms accepted in the art (see e.g. Leahy 1986). The reference solvent for these experiments is water (e.g. $K_{m/water}$).

A strength of this approach is that once the MCF system constants are known and molecular descriptors determined for a compound, the effects of mixture chemicals, solvents, or formulation additives can be easily tested by directly assessing apparent changes in the descriptors (denoted as $\delta$) for specific fibers compared to the aqueous reference data. Since the molecular descriptors are also linked to IPPSF absorption profiles, mixture- or solvent-induced changes detected in the MCF studies can be directly mapped onto the corresponding descriptors in the QSPR relationship defining the IPPSF data to assess the significance of specific interactions on dermal absorption.

Three experimental phases are employed in the MCF approach: (1) calibration of the system constants for each MCF with compounds of known molecular descriptor values [R, $\pi$, $\alpha$, $\beta$, and L]; (2) determination of descriptors for unknown chemicals with the calibrated MCFs; and (3) determination of the mechanisms of interactions involving solvents and chemical mixtures that significantly modulate percutaneous absorption using the calibrated MCFs. These apparent descriptors, reflecting the interaction effects, are used to determine the values for [A, b and d] in the IPPSF model. The framework of mixed-effect modeling described below couples the MCF data to a surrogate in vivo IPPSF endpoint.

Example 3-1

Calibration of the MCF System Constants

A series of calibration compounds are used to estimate the system parameters for a specific fiber in the water solvent system. This approach employs the MCF technique to generate descriptors in an aqueous system at 37° C. for subsequent use in evaluating mixture chemical interactions or solvent effects. Different fibers are selected to model specific types of interactions. For example, in Example 1 above, a polydimethylsiloxane (PDMS, silicone) MCF fiber was used to estimate $K_{octanol/water}$. However, silicone is biased toward hydrophobic interactions and could only be sensitive to mixture effects involving these classes of skin constituents. Additional partition coefficients are utilized to obtain better in vivo predictions as well as to detect more subtle chemical mixture or solvent interactions that can be biologically relevant to altered dermal absorption.

To get reasonable estimates of all system constants, fibers and compounds are selected which are sensitive to widely varying physical chemical properties. Fifteen different membrane coated fibers tabulated below are studied. Membrane materials are selected based on current knowledge of chromatographic stationary phases (Table II). The selection is made by covering wide ranges of intermolecular forces (R, $\pi$, $\alpha$, $\beta$, and L) as reflected in varying strength coefficients that scale these forces to a fiber's log $K_{m/s}$. C18 is also selected, as it is the most used HPLC stationary phase, and it offers low polar, but high hydrophobic (dispersion) interactions.

TABLE II

Selection of Membrane Materials

| # | Material | Abbr. | c | r | s | a | b | l |
|---|---|---|---|---|---|---|---|---|
| 1 | Poly(methylsiloxane)(4-butanephenyl)-hexafluoropropan-2-ol | PSF6 | −0.510 | −0.360 | 0.820 | 0.000 | 1.110 | 0.540 |
| 2 | Poly(dimethylsiloxane) | PDMS | −0.194 | 0.024 | 0.190 | 0.125 | 0.000 | 0.498 |
| 3 | Poly(dimethylmetbylphenylsiloxane) (10 mol % phenyl) | OV-3 | −0.181 | 0.033 | 0.328 | 0.152 | 0.000 | 0.503 |
| 4 | Poly(methylphenyldiphenylsiloxane) (75 mol % phenyl) | OV-25 | −0.273 | 0.277 | 0.644 | 0.182 | 0.000 | 0.472 |
| 5 | Poly(trifluoropropylmethylsiloxane) | QF-1 | −0.269 | −0.449 | 1.157 | 0.187 | 0.000 | 0.419 |
| 6 | Poly(methylphenylsiloxane) | OV-17 | −0.372 | 0.071 | 0.653 | 0.263 | 0.000 | 0.518 |
| 7 | Poly(cyanopropylmethyldimethylsiloxane) | OV-105 | −0.203 | 0.000 | 0.364 | 0.407 | 0.000 | 0.496 |
| 8 | Poly(cyanopropylmethylphenylmethylsiloxane) | OV-225 | −0.541 | 0.000 | 1.226 | 1.065 | 0.000 | 0.466 |
| 9 | Poly(ethylene glycol) | U50HB | −0.184 | 0.372 | 0.632 | 1.277 | 0.000 | 0.499 |
| 10 | Poly(dimethylsiloxane)/carbowax copolymer | OV-330 | −0.430 | 0.104 | 1.056 | 1.419 | 0.000 | 0.481 |
| 11 | Poly(dicyanoallylsiloxane) | OV-275 | −0.909 | 0.206 | 2.080 | 1.986 | 0.000 | 0.294 |
| 12 | Poly(diethylene glycol succinate) | DEGS | −0.669 | 0.197 | 1.668 | 2.246 | 0.000 | 0.411 |
| 13 | Polydimethylsiloxane/divinylbenzene | PDMS/DVB | — | — | — | — | — | — |
| 14 | Carbowax/divinylbenzene | CW/DVB | — | — | — | — | — | — |
| 15 | Polyacrylate | PA | — | — | — | — | — | — |

Data in Table II are those available from Abraham et al. (1999) determined using GC. Fibers 13-15 are commercially available but have not been parameterized.

Preparation of the Membrane Coated Fibers: Polysiloxane and polyethylene glycol (PEG) polymers are the primary stationary phases used in modern gas chromatography. These two polymers can be crosslinked and uniformly coated onto the surfaces of fused-silica fibers or inside of the capillary columns. The physiochemical properties of these two polymers can be easily modified by integrating different functional groups into the polymer backbones.

The membrane-coated fibers can be prepared using any preparation technique that is generally suitable for preparing a stationary phase in gas chromatography, as would be apparent to one of ordinary skill in the art after a review of the present disclosure. Two representative methods are as follows. The first method is to coat the membrane on a section of fused-silica fiber as used in Examples 1 and 2. Four MCFs (#2, 13-15 in Table II) of this type are commercially available for use in solid-phase extractions. The PEG polymer based MCFs in Table III are prepared with a sol-gel technology developed by Wang et al. (2000). The functionally modified PEG backbone with end-hydroxyl groups is integrated into the sol-gel matrix to form a thermal and chemical stable cross-linked membrane. The polysiloxane based MCFs (#3-#8 in Table II) are prepared with procedures developed by Lee and coworkers (Peaden at al. 1982; Kong et al. 1984). The polysiloxane polymer with given ratios of functional groups and 1% vinyl-polysiloxane is coated on to an inert fiber (fused-silica or stainless steel), then the polymer is crosslinked by the vinyl groups initiated by radicals. PSF6 (#1 in Table II) is a hydrogen-bond acid stationary phase developed by Martin, Pool et al. (1998), in which the polymethylsiloxane backbone comprises 4-butanephenyl and hexafluoropropanol-2.

The second method employs a section of the GC capillary column and mounts it inside a stainless needle, which is modified to allow compounds partitioning into the membrane inside the capillary tube and desorbing into the GC injector for quantitative analysis. Such capillary columns are commercially available for all of the membrane materials in Table II except #1.

Calibration Compounds: Fifty calibration compounds with known molecular descriptors of varying physical chemical properties are selected (Table III). Some of the molecules are chosen to have extreme values (e.g. 0) in the descriptor matrix, which significantly increases the statistical power of the study. These compounds were selected as being amenable to GC/MS analysis and have known molecular descriptor values.

TABLE III

Calibration Compounds

| # | Solute | $R_2$ | $\pi$ | $\alpha$ | $\beta$ | $\log L^{16}$ |
|---|---|---|---|---|---|---|
| 1 | 2,2,2-Trifluoroethanol | 0.015 | 0.60 | 0.57 | 0.25 | 1.224 |
| 2 | 2-Fluorophenol | 0.660 | 0.69 | 0.61 | 0.26 | 3.453 |
| 3 | 2-Methoxyphenol | 0.837 | 0.91 | 0.22 | 0.52 | 4.449 |
| 4 | 2-Naphthol | 1.520 | 1.08 | 0.61 | 0.40 | 6.200 |
| 5 | 3-Cyanophenol | 0.930 | 1.55 | 0.77 | 0.28 | 5.181 |
| 6 | 3-Nitrotoluene | 0.874 | 1.10 | 0.00 | 0.25 | 5.097 |
| 7 | 4-Chlorophenol | 0.915 | 1.08 | 0.67 | 0.20 | 4.775 |
| 8 | 4-Cyanophenol | 0.940 | 1.63 | 0.79 | 0.29 | 5.420 |
| 9 | 4-Fluorophenol | 0.670 | 0.97 | 0.63 | 0.23 | 3.844 |
| 10 | 4-Iodophenol | 1.380 | 1.22 | 0.68 | 0.20 | 5.492 |
| 11 | 4-Nitrophenol | 1.070 | 1.72 | 0.82 | 0.26 | 5.876 |
| 12 | 4-Nitrotoluene | 0.870 | 1.11 | 0.00 | 0.28 | 5.154 |
| 13 | Benzene | 0.610 | 0.52 | 0.00 | 0.14 | 2.786 |
| 14 | Benzyl alcohol | 0.803 | 0.87 | 0.33 | 0.56 | 4.221 |
| 15 | Biphenyl | 1.360 | 0.99 | 0.00 | 0.22 | 6.014 |
| 16 | 1,2-Dichloroethene | 0.436 | 0.61 | 0.11 | 0.05 | 2.439 |
| 17 | Cyclohexane | 0.305 | 0.10 | 0.00 | 0.00 | 2.964 |
| 18 | Cyclohexanol | 0.460 | 0.54 | 0.32 | 0.57 | 3.758 |
| 19 | Cyclooctane | 0.413 | 0.10 | 0.00 | 0.00 | 4.329 |
| 20 | Dibenzothiophen | 1.959 | 1.31 | 0.00 | 0.18 | 7.575 |
| 21 | Dichloromethane | 0.387 | 0.57 | 0.10 | 0.05 | 2.019 |
| 22 | Diethylether | 0.041 | 0.25 | 0.00 | 0.45 | 2.015 |
| 23 | Dimethyl phthalate | 0.780 | 1.41 | 0.00 | 0.88 | 6.051 |
| 24 | Di-n-butyether | 0.000 | 0.25 | 0.00 | 0.45 | 3.924 |
| 25 | Di-n-butylamine | 0.107 | 0.30 | 0.08 | 0.69 | 4.349 |
| 26 | 1-Dodecanol | 0.175 | 0.42 | 0.37 | 0.48 | 6.640 |
| 27 | Ethylamine | 0.236 | 0.35 | 0.16 | 0.61 | 1.677 |
| 28 | Ethylphenylketone | 0.804 | 0.95 | 0.00 | 0.51 | 4.971 |
| 29 | Fluoroethane | 0.052 | 0.35 | 0.00 | 0.10 | 0.559 |

TABLE III-continued

Calibration Compounds

| # | Solute | $R_2$ | $\pi$ | $\alpha$ | $\beta$ | $\log L^{16}$ |
|---|---|---|---|---|---|---|
| 30 | 1-Hexafluoropropanol | −0.240 | 0.55 | 0.77 | 0.10 | 1.392 |
| 31 | Hexamethylbenzene | 0.950 | 0.72 | 0.00 | 0.21 | 6.557 |
| 32 | 1-Chlorohexane | 0.201 | 0.40 | 0.00 | 0.10 | 3.777 |
| 33 | 1-Chlorooctane | 0.191 | 0.40 | 0.00 | 0.10 | 4.772 |
| 34 | 1-Fluorohexane | 0.000 | 0.35 | 0.00 | 0.10 | 2.951 |
| 35 | Methanol | 0.278 | 0.44 | 0.43 | 0.47 | 0.970 |
| 36 | N,N-Dimethylacetamide | 0.363 | 1.33 | 0.00 | 0.78 | 3.717 |
| 37 | Naphthalene | 1.340 | 0.92 | 0.00 | 0.20 | 5.161 |
| 38 | n-Butylamine | 0.224 | 0.35 | 0.16 | 0.61 | 2.618 |
| 39 | o-Cresol | 0.840 | 0.86 | 0.52 | 0.30 | 4.218 |
| 40 | 1-Pentanol | 0.219 | 0.42 | 0.37 | 0.48 | 3.106 |
| 41 | Phenanthrene | 2.055 | 1.29 | 0.00 | 0.26 | 7.632 |
| 42 | Phenol | 0.805 | 0.89 | 0.60 | 0.30 | 3.766 |
| 43 | Piperidine | 0.422 | 0.46 | 0.10 | 0.69 | 3.304 |
| 44 | Tetrachloromethane | 0.458 | 0.38 | 0.00 | 0.00 | 2.823 |
| 45 | Thiophenol | 1.000 | 0.80 | 0.09 | 0.16 | 4.110 |
| 46 | Trichloromethane | 0.425 | 0.49 | 0.15 | 0.02 | 2.480 |
| 47 | Triethyl phosphate | 0.000 | 1.00 | 0.00 | 1.06 | 4.750 |
| 48 | Triethylamine | 0.101 | 0.15 | 0.00 | 0.79 | 3.040 |
| 49 | Trimethylamine | 0.140 | 0.20 | 0.00 | 0.67 | 1.620 |
| 50 | 1-Undecanol | 0.181 | 0.42 | 0.37 | 0.48 | 6.130 |

Extreme values within columns are bold faced.

The molecular descriptors [R, π, α, β, V and L] are properties of the specific solute, will not change with the membrane/solvent systems. In this calibration phase, only water is employed as a solvent (s=water), as this is most biologically relevant to the dermal absorption problem at hand. All studies are conducted at 37° C. Thus, for each fiber, fifty equations (n=50 compounds) are generated from the model (Eq. 4) as follows:

$$\log K_{m/s}^n = c + rR^n + s\pi^n + a\alpha^n + b\beta^n + vV^n + l \log L^n \quad (\text{Eq. 7})$$

Each 50 fiber/solute experiment is replicated 6 times. Based on Examples 1 and 2, this number of replicates should result in a sample coefficient of variation of response of ≦3%. The system constants [c, r, s, a, b, v and l] are obtained via multiple linear regression analysis of this equation 7 matrix for each fiber (SAS, Cary, N. C., United States of America). These strength constants are employed in estimating [R, π, α, β, V and L] for the 40 study chemicals in Example 3-2 below.

Example 3-2

Determination of Molecular Descriptors for Solute Penetrants of Interest

Once the system constants [c, r, s, a, b, v and l] are obtained for each membrane/solvent system, they are employed in a second phase to determine molecular descriptors for study chemicals. The system constants (e.g. strength coefficients) are properties of the membrane/solvent system, and will not change with different solutes. This provides for the determination of the molecular descriptor for any unknown solute by simply measuring its partition coefficient with each fiber. For example, for a solute of unknown descriptors [R, π, α, β, V and L], fifteen equations (m=15) are generated from the model equation 4 from each of 15 different fibers each with a different set of system constants:

$$\log K_{m/s} = c_m + r_m R + s_m \pi + a_m \alpha + b_m \beta + v_m V + l_m \log L \quad (\text{Eq. 8})$$

Multiple linear regression analysis of this matrix of equations provides the molecular descriptors for the compound. In this regression problem, the system constants (c, r, s, a, b, v, l)$_{m/s}$ are known parameters for each fiber and now [R, π, α, β, L and V] are the estimated parameters. The purpose of estimating these descriptors is to generate values for parameterizing the IPPSF model and providing reference descriptors in water as a solvent to subsequently detect chemical mixture or solvent interactions. It is assumed that such interactions would not be reflected in changes in the intrinsic molecular volume (V). Thus, to simplify further statistical analysis to the determination of five descriptors, the fiber's system parameters [$c_m$ and $v_m$] as well as the intrinsic volume [V] are collapsed into a new fixed fiber system parameter termed Z where:

$$Z_m = c_m + v_m V \quad (\text{Eq. 9})$$

Equation 8 above thus reduces to:

$$\log K_{m/s} = Z + r_m R + s_m \pi + a_m \alpha + b_m \beta + l_m \log L \quad (\text{Eq. 10})$$

Study Compounds: The compounds selected to be parameterized are those that are also used to study percutaneous absorption in additional MCF and IPPSF experiments. Table IV lists the 40 chemicals selected for this purpose.

TABLE IV

Study Compounds

| # | Compound | logKo/w | MW |
|---|---|---|---|
| 1 | Dimethyl sulfoxide | −1.35 | 78.13 |
| 2 | 1,3,5-triazine | −1.17 | 171.29 |
| 3 | 1,4-dioxane | −0.27 | 88.11 |
| 4 | Theophylline | −0.02 | 180.17 |
| 5 | Diethylamine | 0.58 | 73.14 |
| 6 | methyl nicotinate | 0.64 | 137.14 |
| 7 | Resorcinol | 0.8 | 110.11 |
| 8 | 4-aminobenzoic acid | 0.83 | 137.14 |
| 9 | 1-nitropropane | 0.87 | 89.10 |
| 10 | n-butanol | 0.88 | 74.12 |
| 11 | Aniline | 0.90 | 93.13 |
| 12 | 2-pentanone | 0.91 | 86.14 |
| 13 | 4-methyl-2-pentanone | 1.31 | 100.16 |
| 14 | Phenol | 1.46 | 94.11 |
| 15 | 4-nitrophenol | 1.91 | 139.11 |
| 16 | m-cresol | 1.95 | 108.14 |
| 17 | Benzene | 2.13 | 78.12 |
| 18 | salicylic acid | 2.26 | 138.12 |
| 19 | dimethylaniline | 2.31 | 121.18 |
| 20 | Carbaryl | 2.36 | 201.23 |
| 21 | 4-chlorophenol | 2.39 | 128.56 |
| 22 | methyl salicylate | 2.55 | 152.15 |
| 23 | Atrazine | 2.61 | 215.69 |
| 24 | 1,8-cineole | 2.74 | 154.25 |
| 25 | 4-nitroethylbenzene | 3.03 | 151.17 |
| 26 | 1-iodobutane | 3.08 | 184.02 |
| 27 | m-xylene | 3.20 | 106.17 |
| 28 | Naphthalene | 3.30 | 128.18 |
| 29 | Chloroneb | 3.44 | 207.06 |
| 30 | Lindane | 3.72 | 290.83 |
| 31 | Parathion | 3.83 | 291.26 |
| 32 | endosulfan II | 3.83 | 406.93 |
| 33 | Dacthal | 4.28 | 331.97 |
| 34 | Anthracene | 4.45 | 178.24 |
| 35 | Chlorobenzilate | 4.74 | 325.19 |
| 36 | heptachlor epoxide | 4.98 | 389.32 |
| 37 | Methoxychlor | 5.08 | 345.66 |
| 38 | Pentachlorophenol | 5.12 | 266.34 |
| 39 | Nonylphenol | 5.99 | 220.36 |
| 40 | Laurocapram | 6.28 | 281.49 |

It is important to note that values of the molecular descriptors [R, π, α, β, and L] are not readily or reliably available in the art for chemicals of toxicological (e.g. pesticides) or practical (e.g. drugs) significance. This supports a further utility of the data generated here. The selected compounds have structural diversity and range in molecular weight from 73 to 406 and log $K_{o/w}$ from −1.35 to 6.28. Included in these compounds are some with known biological activity in skin effectively acting as positive controls that are known to significantly alter absorption of some penetrants (e.g. DMSO, laurocapram—AZONE®, and the terpene 1,8-cineole) (Walters, 1989; Williams and Barry, 1998). Methyl nicotinate (MNA) is a known vasodilator. These compounds are included as their rate and extent of percutaneous absorption could be strongly influenced by their activity in skin.

Some compounds that have biological relevance (e.g. steroids, some drugs) cannot be studied using GC/MS. This is not a significant constraint for the long-term application of this approach as the chemicals partitioned into a MCF can also be analyzed by LC/MS or IR spectroscopy. The same sets of molecular descriptors can then be utilized. However, the present configuration is designed to use the MCF as the injection fiber in a GC/MS to reduce calibration and experimental time to a more manageable level. Forty compounds are studied in all 15 fibers (n=3-9 replicates) to generate values of [R, $\pi$, $\alpha$, $\beta$, and L] for parameterization (along with V) of the IPPSF studies and assessment of mixture interactions. The number of replicates is dependent upon the magnitude of the differences between the MCF properties.

Optimal Fiber Selection: Optionally, each chemical should be studied in 15 fibers as formulated above. However, the complexity of the experimental system is reduced to one of more manageable proportions when used in the chemical and solvent interaction Examples. The above system calibration matrix is statistically analyzed using step-wise subtraction of fiber vectors as well as a principal component analysis from the regression matrix to determine the minimal number of fibers that contribute adequate predictability to determine the five system parameters. A maximum of eight fibers are selected to determine the molecular descriptors of the study chemicals. These eight fibers are then used as a base experimental system for MCF studies involving solvent and mixture effects.

It is also possible that where the 15 fiber matrix is analyzed for 40 chemicals, results of this correlation analysis could indicate that one or more of the above molecular descriptors [R, $\pi$, $\alpha$, $\beta$, and L] is redundant (e.g. highly correlated to a different parameter) and does not offer significant statistical power in determining fiber partition coefficients. In this case, a process similar to the formulation of the Z parameter is conducted to collapse the variable into constant Z. This is addressed by step-wise regression techniques, which reduce the number of parameters estimated in subsequent phases of this Example.

The use of a smaller number of fibers reduces the statistical power of this analysis, which is a function of both number of replicates and the magnitude of the value of system constants among fibers. However, for the purposes of dermal absorption studies, it is equally important to reduce experimental complexity to one of manageable proportions. Secondly, an experimental paradigm that allows detection of significant mixture interactions is also part of the approach of this Example. Thus, data from a maximum of eight fiber systems is used to estimate the value of the five molecular descriptors. Viewed from the perspective of current practice in the art, which predicts percutaneous absorption using only $K_{o/w}$, or at most two different partition coefficients ($\Delta$ log $K_{oct-dce}$) (Geinoz et al., 2002), or experimentally determined a permeability coefficient in a single membrane system; the MCF approach is significantly more robust.

Final Chemical Selection: This phase generates a matrix of molecular descriptors for the 40 study chemicals. Parallel to these studies, data are also obtained on IL-8 release and FTIR shifts for these 40 chemicals. Twenty chemicals are studied in Example 3-3. Compounds with as wide as possible range for molecular descriptors [R, $\pi$, $\alpha$, $\beta$, V and L] are selected. In contrast, some compounds with similar molecular descriptors are also selected to test the sensitivity, which is to control for compounds with minimal differences in descriptors. Compounds are also included that cause significant IL-8 release or shifts in FTIR.

Example 3-3

Determination of Solvent and Mixture Effects

Mixture and vehicle effects are also considered when evaluating percutaneous absorption of a compound. At present, there is no straightforward method to assess these effects quantitatively, nor link them to the molecular interactions embodied in the molecular descriptors above that are routinely used to predict dermal absorption. This Example provides a method to quantitatively assess the mixture and vehicle effects using the solute descriptors obtained from the MCF technique.

The eight fibers selected in Example 3-2 above cover a wide strength range of intermolecular interactions. The system constants are determined for each fiber in Example 3-1 in water, where no solute-solute intermolecular interactions exist outside of the solute-membrane and solute-water interactions. The system constants determined under such ideal conditions are set as the reference point for assessment of solvent and mixture effects, and are denoted as $[Z,r,s,a,b,l]°_{m/water}$. When additional solutes are added, solute-solute interactions are expected to occur. Similarly, if a solvent is added into the system, solvent-solute interactions will occur. In the MCF system, this is reflected in an altered partition coefficient for fibers whose properties are sensitive to these types of molecular interactions. These effects could occur in very complex pattern.

To approach this problem, the membrane/water system constants $[Z,r,s,a,b,l]°_{m/water}$ are defined as a reference point. For a given compound with descriptors (R,$\pi$,$\alpha$,$\beta$,V,L), its partition coefficient in the mixture or solvent solution is measured using the eight fibers selected above (log $K_{m/mix}$, m=8). The partition coefficient (log $K_{m/mix}$) and the reference system strength constants $[Z,r,s,a,b,l]°_{m/water}$ for each fiber are used to generate the regression equation matrix (similar to Eq. 10, while m=8). Again, it is assumed that effects linked to V will not be significant and thus it is incorporated into the fixed Z as described above for each solute in the 8 membranes. Multiple linear regression analysis of the matrix generates a set of apparent molecular descriptors (R',$\pi$',$\alpha$',$\beta$',L').

These apparent descriptors carry all the information of the mixture and/or solvent effects. In reality, log $K_{m/mix}$ is changing because the fiber system strength constants [r,s,a,b,l] are changing in these exposure scenarios. One could denote these changes as ($\Delta$r, $\Delta$s, $\Delta$a, $\Delta$b, $\Delta$l) and rewrite equation for a mixture- or solvent-interaction study as:

$$\text{Log } K_{m/s}(\text{interaction})=Z+r_m(\Delta rR)+s_m(\Delta s\pi)+a_m(\Delta a\alpha)+b_m(\Delta b\beta)+l_m(\Delta l \log L) \quad \text{(Eq. 11)}$$

Operationally the values are defined in the parenthesis as the apparent molecular descriptors (R',$\pi$',$\alpha$',$\beta$',L'). For computational simplicity and to clearly assign interactions to the relevant molecular property, these changes linked to the molecular descriptors are described as $\delta$ values. The interactions can then be quantitatively described by subtraction of the reference from the apparent descriptors to generate δ values reflecting the pure mixture effects: (δR, δπ, δα, δβ, δL)=(R', π',α',β',L')−(R,π,α,β,L). The δ parameters reflect the altered strength coefficients (Δ) for each descriptor secondary to the mixture or solvent effect, and are used here to facilitate discussion of these interactions independent of the MCF experimental context that generated them. This distinction is a tool to aid in their subsequent interpretation in the mixture and solvent experiments, as well as in the final biological IPPSF absorption model.

The apparent molecular descriptors [R',π',α',β',L'] correlate to solvation energy related physiochemical properties (e.g. partition coefficient, permeation constant; solubility) since they reflect all of the intermolecular interactions in the mixture. The apparent descriptors are obtained in the MCF interaction experiments. In this framework, these apparent descriptors are used to parameterize [A, b, d] in the IPPSF model after mixture or solvent exposures.

Solvent Effects: Five solvent systems are employed to probe potential interactions compared to the water reference system. These include 50% water/50% ethanol (the second solvent systems used in the IPPSF exposures) as well as 100% ethanol; 100% acetone; 100% cyclohexane; and 100% propylene glycol. The selection of test solvents is based in part on two different criteria: (1) relevance to dermal absorption; and (2) chemical property dissimilarity to "force" significant descriptor interactions to occur. Ethanol, aqueous ethanol and acetone were selected because similar solvents have been often used in human and laboratory animal studies (Cross et al., 2001; Zatz, 1993), including mixture interaction experiments that demonstrated significant modulation of in vivo absorption (see e.g. Brooks and Riviere, 1996; Baynes and Riviere, 1998). Cyclohexane has also been employed as a solvent in topical exposures (King and Monteiro-Riviere, 1991) and provides a different physical chemical environment to test the solute descriptors.

The 20 compounds selected in Example 3-2 above are studied for a total of 20 chemicals×5 solvents or 100 experiments conducted in all eight fibers with 3-9 replicates, for reasons similar to that discussed in Example 3-2. This phase generates a series of (δR, δπ, δα, δβ, δL)$_{solvent}$ which can be evaluated to determine those solvent/solute combinations which have the largest effects on absorption.

Mixture Effects: A number of binary and multi-component mixtures (2, 4, 8, 12, 16 and 20 components) are created from the 20 compounds selected above for IPPSF studies. Doses of mixture components are titrated to produce a significant δ for the chemical being monitored. Those mixtures providing the largest (δR, δπ, δα, δβ, δL)$_{mixture}$ values are selected for IPPSF studies described in Example 4 below. This is a strength of the MCF fiber technique as the IPPSF studies probe the values of δ that significantly change percutaneous absorption. Additionally, since this approach links the solvent/solute mixture interactions to specific molecular descriptors, mechanisms of interactions that significantly alter absorption can be described.

As in the solvent experiments, mixtures are composed from the set of 20 chemicals selected in Example 3-2. Eighty experimental mixtures are randomly determined and spread over 2, 4, 8, 12, 16 and 20 (total mixture) combinations. Compass plots (Budsaba et al., 2000) and other graphical screening tools are used to determine the most prominent mixture effects.

Example 4

IPPSF Experiments

The IPPSF technique, described herein above, is employed in this Example.

Mixed Effect Modeling: Mixed effects modeling is used to identify and characterize factors that alter the cutaneous absorption of toxic substances in chemical mixtures. This modeling technique makes it possible to identify sources of variability, particularly if there is a broad range of factors of potential relevance with unknown relationships present. Physical chemical interactions that alter salvation properties, detected in MCF studies, as well as biologically based interactions are expected to affect the absorption of chemicals in the IPPSF. Mixed effects modeling can be used as a tool to identify and characterize these interactions.

Perfusate flux-time data (Y(t)) obtained from the IPPSF experiments is fitted to the previously defined bi-exponential structural model (Eq. 5) using non-linear regression:

$$Y(t)=A(e^{-bt}-e^{-dt}) \quad \text{(Eq. 12)}$$

This model predicts values for the flux of a chemical compound at a certain time. Parameter A relates to the amount of applied dose ultimately absorbed, parameter b reflects the rate of terminal release of the absorbed chemical and parameter d reflects the rate of uptake of the chemical from the skin surface. Mixed-effect modeling has been widely applied in human clinical pharmacology for decades (Sheiner and Beal, 1980, 1981, 1983) and is now embodied in the commercially available software package marketed under the trademark WINNONMIX® (Pharsight Corporation, Cary, N. C., United States of America).

The predicted values for the flux of a chemical compound differ from measured values. In a mixed effects model, these differences are attributed to both fixed and random effects. Predictions should be improved if parameters A, b and d are calculated more accurately by accounting for a number of fixed effects that reflect both physico-chemical and biologically based interactions. This can be done by considering both solute descriptors [R', α', β', π', V' and log L'] as well as indicators of biological activity (IL8 release from keratinocyte cell cultures and shifts in FTIR stratum corneum spectra) as co-variates in the mixed effect model, in the following manner:

$$A_{avg} = \theta_1 + \theta_2 R' + \theta_3 \pi' + \theta_4 \alpha' + \theta_5 \beta' + \theta_6 V' + \\ \theta_7 \log L' + \theta_8 (\Delta IL8 \text{ release}) + \theta_9 (\Delta FTIR \text{ spectrum}) \quad \text{(Eq. 13)}$$

$$b_{avg} = \theta_{10} + \theta_{11} R' + \theta_{12} \pi' + \theta_{13} \alpha' + \theta_{14} \beta' + \theta_{15} V' + \\ \theta_{16} \log L' + \theta_{17} (\Delta IL8 \text{ release}) + \theta_{18} (\Delta FTIR \text{ spectrum}) \quad \text{(Eq. 14)}$$

$$d_{avg} = \theta_{19} + \theta_{20} R' + \theta_{21} \pi' + \theta_{22} \alpha' + \theta_{23} \beta' + \theta_{24} V' + \\ \theta_{25} \log L' + \theta_{26} (\Delta IL8 \text{ release}) + \theta_{27} (\Delta FTIR \text{ spectrum}) \quad \text{(Eq. 15)}$$

Initial values for the theta (θ) coefficients of the covariates are estimated by stepwise correlation with the molecular descriptors using multiple regression analysis, performed as described herein above. Note that in the water reference MCF studies, the apparent descriptors are the reference descriptors (δ=0).

ΔIL8 release and ΔFTIR will be measured from control conditions with no solute or solvent present. The majority of chemicals result in zero values for ΔIL8 release and ΔFTIR, eliminating these two parameters from the correlation matrix. Finally, parallel to the correlation analysis in MCF Phase II above, this analysis can determine that not all molecular descriptors are required to predict [A, b, d] as some might be significantly correlated to one another. If this occurs, then these parameters do not offer sufficient information to be included as individual variables in this analysis and they are combined. This can be addressed with step-wise regression techniques. Despite more accurate prediction, residual inter- and intra-individual variability occurs. These are attributed to random effects and quantified as:

$Y_{ij}(t) = Yi(t) + \epsilon_{ij}$ (with variance of $\epsilon = \sigma^2$) (Eq. 16)

$A_j = A_{avg} + \eta_{Aj}$ (with variance of $\eta_{Aj} = \omega^2_A$) (Eq. 17)

$d_j = d_{avg} + \eta_{dj}$ (with variance of $\eta_{dj} = \omega^2_d$) (Eq. 18)

$b_j = b_{avg} + \eta_{bj}$ (with variance of $\eta_{bj} = \omega^2_b$) (Eq. 19)

This model is fit using the 20 study compounds selected from Example 3-2 dosed in both water and ethanol/water vehicles. In ethanol/water, the apparent descriptors [R',π',α'β',L'] and V, which reflect the potential ethanol effects, are used to establish the θ correlation matrix. θ is independent of any solvent effects, as this information is embedded in the apparent descriptors. Lack of fit is reflected in η. This design yields 40 IPPSF treatments replicated 4 times (160 IPPSFs).

Nonlinear mixed effects modeling are performed using the commercially available software program WINNONMIX® (Pharsight Corporation). This program offers a number of different algorithms and regression techniques that can be used to estimate parameters and their variability. The first step involves specifying the structural pharmacokinetic model (in this case, the bi-exponential model described above). The program has the capability to consider a total of 36 different fixed effects parameters to improve the estimation of population pharmacokinetic parameters. The relationship of these fixed effects parameters to the pharmacokinetic parameters can be described by means of linear, multiplicative, exponential and logarithmic equations. "Goodness of fit" is reflected in a statistically significant decrease in the minimum value of the objective function (MVOF). Other criteria such as Akaike's Information Criterion (AIC) and Schwarz's Bayesian Criterion (SBC) are also evaluated. Model building is approached in an iterative manner by adding/changing fixed effects parameters and determining how this improves/weakens the model. Normal distribution is assumed and parametric techniques are used to calculate variances. Ideally, identifying and correctly characterizing as many covariates as possible and accounting for these in the fixed effects minimize random effects.

As modeling proceeds, if the values of the variance (η) are large for specific chemicals, this would suggest another factor or biological modifier is present (e.g. vasoactivity) that might have to be included as an indicator (+/−) variable. All perfusate samples are analyzed using GC/MS that allows for detection of metabolites. As discussed herein above, compounds must first pass the stratum corneum before they are accessible for drug metabolism. In these scenarios, total penetrating activity driving diffusion (parent drug and metabolite) is used in the analysis, and any deviation from predicted concentrations is allocated to metabolism.

IPPSF Experimental Designs: Studies are conducted occluded with ethanol and ethanol-water dosing solutions applied at a concentration of 40 μg/cm² to a 5 cm² surface area. The two vehicles provide altered absorbed dose information for the mixed effect model. These conditions also simulate fiber exposures as well as provide a link to existing IPPSF data and to other in vitro and in vivo exposures in the art. Perfusate samples are collected for 8 hours (0, 10, 20, 30, 45 60 75 and 90 min, and every ½ h until termination at 8 h). All samples are analyzed for compound absorption using GC/MS. Treatments are repeated in 4 flaps, and this number has been shown to be an efficient number for statistical comparisons. This allows for calculation of a variance for the error term in the mixed effects model described below.

Example 4-1

Model Parameterization

IPPSF absorption studies are conducted to define the [A, b, d] model using mixed effect modeling techniques disclosed above. To control costs, twenty chemicals are used to formulate the mixed effect model relating the molecular descriptors [R, π, α, β, V, and log L] to the IPPSF model parameters [A, b and d]. This results in an n of 4 flaps per treatment in two vehicles (ethanol, ethanol-water) for 20 chemicals for a total of 160 flaps. Compounds are dosed occluded at the reference concentration (40 μg/cm²) used in previous IPPSF experiments and in many in vivo human studies so that a link exists to the art. Existing IPPSF datasets for other compounds previously studied are not appropriate to use in this analysis since the compound flux has often been assayed using radioactive tracers, and not GC-MS as describe herein.

Example 4-2

Mixture and Solvent Effects

The flux of a chemical compound of interest in a complex chemical mixture, formulation, or different solvent system should be precisely predicted by using a similar mixed effect modeling technique. In this case, model parameters use the apparent molecular descriptors [R',π',α',β',L'] and V as used for the ethanol/water exposures. Biological effects of the complex chemical mixture being studied are accounted for in a similar manner using biological co-variates [FTIR shifts, IL-8 release] as disclosed herein. Residual variability is modeled to quantitate unexplained interactions. For example, ionic interactions or chemical reactions between mixture constituents can occur which are detectable in the MCF, but not easily quantifiable or assignable by solvation energy relationships (e.g. Δr and Δs in an MCF experiment would not map to δR or δπ). An additional term, considering the MCF constants, is computed to account for this.

Twenty additional chemical/solvent pairs are selected based upon the results of Example 3-3 solvent experiments that suggest significant changes in membrane partitioning phenomenon to explore solvent effects. These selections are based on examining the (δR, δπ, δα, δβ, δL)$_{solvent}$ values obtained. With four replicates per experiment, this results in an additional 80 IPPSF experiments. Finally, 25 different component mixtures (n=4 flaps/treatment; 100 IPPSFs) are selected based on the data generated in the Example 3-3 mixture experiments studied by selecting 2, 4, 8, 12, 16 and 20 component mixtures (n=6 mixtures of each size) whose components are those determined to have the largest values of $(\delta R, \delta \pi, \delta \alpha, \delta \beta, \delta L)_{mixture}$.

Example 4-3

Biomarkers

The approach to assessing significant chemical interactions in the IPPSF methodology is via correlation of altered IPPSF profiles to independently measured biomarkers. Release of the cytokine IL-8 from epidermal keratinocyte cell cultures is a sensitive but broad biomarker for chemical-induced irritation (Allen et al., 2000, 2001a, b; Chou et al., 2002, Zhang et al., 1995). Porcine keratinocytes are used to be comparable with the IPPSF. A chemical's ability to alter lipid permeability is assessed using FTIR as it reflects changes in lipid permeability induced by chemical enhancers. Both of these changes are expressed as change from control solvent exposure for the treatment being studied. If these biomarkers of irritation or permeability do not correlate to changes in IPPSF profiles, alternative biomarkers can be adopted.

IL-8 Release Methods in Keratinocyte Cell Cultures. IL-8 release is assessed according to the standardized technique utilized by Allen et al., 2000, 2001a, b; Chou et al., 2002, and/or Zhang et al., 1995. Briefly, pig skin is obtained from pigs used to generate IPPSF that have already been euthanatized. The skin is dermatomed at 400 µm then cut into 2 cm$^2$ pieces, which is floated, dermis side down, on 0.25% trypsin overnight at 4° C. The epidermis is peeled away from the dermis and placed into Dulbecco's Modified Eagle Medium (DMEM) supplemented with 10% fetal bovine serum (FBS). A single cell suspension is achieved by agitating the epidermal pieces with a pipette and filtering the resultant slurry through a 70 µm mesh screen. Porcine keratinocytes are plated onto collagen Type I (Collaborative Research Products)-coated 96 well plates overnight in DMEM.

The media is replaced by a calcium-free keratinocyte basal media (KBM, Clonetics of San Diego, Calif., United States of America) supplemented with human epidermal growth factor (0.1 ng/ml), insulin (5 µg/ml), bovine pituitary extract (0.4%), and 50 µg/ml gentamicin/50 ng/ml amphotericin-B to create keratinocyte growth media (KGM-2, Clonetics). For optimal keratinocyte growth and proliferation, 0.075 mM $CaCl_2$ and 1.0% are added to KGM-2. All cells in the 96 well plates are maintained in a humidified incubator at 37° C. with a 95% $O_2$/5% $CO_2$ atmosphere. Upon reaching 70-80% confluency, fresh KGM-2 and test chemicals will be added to appropriate wells (n=4) for 1-24 hr. Four treatments in quadruplicate at six time points (0, 1, 4, 8, 12, and 24 hrs) are evaluated per plate. Additional control wells at each time point include culture media only. Viability is assessed with neutral red (NR). If the test chemical is not soluble in KGM-2 media, then ethanol that is also used in the IPPSF exposures is employed as it previously has been shown not to affect the results. Although this adds a potential solvent interaction, the purpose of these exposures is to determine if the test compound is capable of causing IL-8 release, and not quantitating the kinetics of release from PEK. Based on previous experiments, the effects of ethanol only treatments are not significantly different than control ($p < 0.05$).

Cytotoxicity is assessed by determining the percentage of viable PEK cells surviving the test chemical/chemical mixture exposure. Cell viability is determined by the NR uptake method. Briefly, 50 µg/ml NR in KGM-2 (NR medium) are pre-incubated at 37° C. overnight and 200 µl is added to the treated wells after sample collection. Following a 3 hour incubation at 37° C. in a 95% $O_2$/5% $CO_2$, the medium will be replaced by 200 µl of wash/fix solution (1% $CaCl_2$ in 0.5% formaldehyde) for 2 min and NR is extracted with 100 µl of 1% acetic acid/49% $H_2O$/50% ethanol. Color formation after 20 min is evaluated by measuring absorption at 550 nm in an ELISA reader (Multiskan™ RC, Labsystem, Helsinki, Finland). Absorbance values are normalized against KGM-2 control wells (maximum viability) and expressed as percent viable relative to control wells. The resulting measurements provide an assessment of total viable biomass in the culture, which is reciprocal to the extent of cytotoxicity.

To determine secreted protein from PEK in response to the test chemicals, a sandwich ELISA assay is used for IL-8. PEK are plated onto 96-well plates as detailed above (n=4). Cells are dosed with the test chemicals and at each time interval following the dose (1, 4, 8, 12, 24 hr), the supernatant is removed and frozen at −80° C. for later assay. Commercial kits for the detection of porcine IL-8 (Biosource, Camarillo, Calif., United States of America) are performed as indicated in the manufacturer instructions. The plates were read at 450 nm on a Multiskan™ RC plate reader (Labsystems, Helsinki, Finland). A recombinant porcine IL-8 is diluted to create a standard reference curve.

FTIR Analysis: FTIR Spectroscopy is well proven for characterizing aspects of weak interactions, especially, the intermolecular interactions studied herein. Two representative approaches can be employed in assessing a compound's interaction with stratum corneum lipids: (1) assessing changes in lipid spectra; or (2) assessing changes in a compounds signature when strongly interacting in a lipid environment. Therefore, FTIR is good second experimental method to verify the results of the MCF technique, and compensate the need for molecular scale understanding the mechanisms of the intermolecular interactions.

Vibrational signals of the functional groups of the study compounds are studied in reference solution or film, stratum corneum and epidermis in order to reveal the intermolecular interactions in the percutaneous absorption. To assess compound induced changes in lipid permeability, IR absorbance shifts of the C-H symmetric and anti-symmetric vibrations associated with stratum corneum lipids are assessed compared to control samples (n=4) (Golden et al., 1986; Potts et al., 1991; Barry et al., 1992). The spectrum shift, $\Delta$(FTIR shift), is determined for an assessment of lipid induced changes. Four replicates per condition are obtained to get a reliable estimate of shift. If the vibrational signal of a compound is interfered by the skin matrix, deuterated compound can be used. The FTIR equipment is a PE Spectrum 1000 with AutoImage™ microscope (available from PerkinElmer Corporation, Wellesley, Mass. United States of America).

Example 4-4

GC-MS Analytical Methods

Quantitative and qualitative analyses are performed on an HP 5890 II gas chromatograph coupled with a HP 5970B mass selective detector (HP—Hewlett Packard Corporation, Palo Alto, Calif., United States of America). An HP 7675 automatic sampler is used to inject 4 µl of the calibration standard solution, while the membrane-coated fibers are injected manually. The injector is maintained at 280° C. for sample vaporization and thermal desorption. Three capillary columns are selected for separation all the calibration compounds and test chemicals (HP-5MS for non-polar and low polar, HP-50 for medium polar and HB-INNOWax for high polar compounds). The separation condition is optimized for resolution and sensitivity. An electronic pressure control is used to maintain a carrier gas flow of 1.00 ml/min helium. The chemicals that permeate into the membrane are qualitatively analyzed in scan-mode. The identification of each compound in the complex mixture was accomplished by using HP CHEMSTATION™ software and matching its fingerprint spectra with a HP MS database. For quantitative analysis, the selected ion monitoring (SIM) mode, and characteristic ions (m/z) are selected for each compound referencing to its spectra acquired experimentally with standard or from MS database. This approach was used to define the MCF technique (Examples 1 and 2 herein above) as well as to assess chemical absorption in porcine skin diffusion cells using the same perfusate composition as the IPPSF (Muhammad et al., 2003).

REFERENCES

The references listed below as well as all references cited in the specification are incorporated herein by reference to the extent that they supplement, explain, provide a background for or teach methodology, techniques and/or compositions employed herein.

Abou-Donia M B, Wilmarth K R, Jensen K F, Oehme K W, Kurt T L. Neurotoxicity resulting from coexposure to pyridostigmine bromide, DEET and permethrin. *J. Toxicol. Environ. Health* 48: 35-56, 1996.

Abraham M H, Chada H S, Martins F, Mitchell R C, Bradbury M W, Gratton J A. Hydrogen bonding part 46: A review of the correlation and prediction of transport properties by an LFER method: physiocochemical properties, brain penetration and skin permeability. *Pestic. Sci.* 55: 78-88, 1999.

Abraham M H, Chada H S, Mitchell R C. The factors that influence skin penetration of solutes. *J. Pharm. Pharmacol.* 47: 8-16, 1995.

Abraham M H, Poole C F, Poole S K. Classification of stationary phases and other materials by gas chromatography. *J. Chromatog. A.* 842: 79-114, 1999.

Abraham M H, Whiting G S, Doherty R M, Shuely W J. Hydrogen Bonding. XVI. A new solute solvation parameter, $\pi_2^H$, from gas chromatographic data. *J. Chromatog.* 587: 213-228, 1991.

Allen D G, Riviere J E, Monteiro-Riviere N A. Analysis of interleukin-8 release from normal human epidermal keratinocytes exposed to aliphatic hydrocarbons: Delivery of hydrocarbons to cell cultures via complexation with α-cyclodextrin. *Toxicol. In Vitro* 15: 663-669, 2001a.

Allen D G, Riviere J E, Monteiro-Riviere N A. Cytokine induction as a measure of cutaneous toxicity in primary and immortalized porcine keratinocytes exposed to jet fuels and their relation to normal human keratinocytes. *Toxicology Letters* 119: 209-217, 2001b.

Allen D G, Riviere J E, Monteiro-Riviere N A. Induction of early biomarkers of inflammation produced by keratinocytes exposed to jet fuels Jet-A, JP-8, and JP-8(100). *J. Biochem. Mol. Toxicol.* 14: 231-237, 2000.

Barratt M D. Quantitative structure-activity relationships for skin permeability. *Toxicology In Vitro* 9: 27-37, 1995.

Barry B W, Edwards H G M, Williams A C. Fourier transform Raman and infrared vibrational study of human skin. Assignment of spectral bands. *J. Raman Spectrosc.* 23: 641, 1992.

Basak S C, Gute B D, Grunwald G, Mills D, Riviere J E, Opitz D. Clustering of JP-8 chemicals using structure spaces and property spaces. A computational approach. *Proc. Int. Conf. Medicinal Chem. Biostatistics*, 1999.

Baynes R E, Brooks J D, Budsaba K, Smith C E, Riviere J E. Mixture Effects of JP-8 additives on the dermal disposition of jet fuel components. *Toxicol. Appl. Pharmacol.* 175: 269-281, 2001.

Baynes R E, Brooks J D, Mumtaz M, Riviere J E. Effects of chemical interactions in pentachlorophenol mixtures on skin and membrane transport. *Toxicol. Sci.* 69: 295-305, 2002b.

Baynes R E, Brooks J D, Riviere J E. Membrane transport of naphthalene and dodecane in jet fuel mixtures. *Tox. Industrial Health* 16: 225-238, 2000.

Baynes R E, Brownie C, Freeman H, Riviere J E. In vitro percutaneous absorption of benzidine in complex mechanistically defined chemical mixtures. *Toxicol. Appl. Pharmacol.* 141: 497-506, 1996.

Baynes R E, Halling K B, Riviere J E. The influence of diethyl-m-toluamide (DEET) on percutaneous absorption of permethrin and carbaryl. *Toxicol. Appl. Pharmacol.* 144: 332-339, 1997.

Baynes R E, Monteiro-Riviere N A, Riviere J E. Pyridostigmine bromide modulates the dermal disposition of [$^{14}$C] permethrin. *Toxicol. Appl. Pharmacol.* 181: 164-173, 2002a.

Baynes R E, Riviere J E. Influence of inert ingredients in pesticide formulations on dermal absorption of carbaryl. *Am. J. Vet. Res.* 59: 168-175, 1998.

Baynes, R. E., Brooks, J. D., Riviere, J. E., Toxicology Industrial Health 16(2000) 225-233.

Blauber B J. The applicability of in vitro-derived data in hazard identification and characterization of chemicals. *Environ. Toxicol. Pharmacol.* 11: 213-225, 2002.

Bliss C I. The toxicity of poisons applied jointly. *Ann. Appl. Biol.* 26: 585-615, 1939.

Bogert C J, Price B, Wells C S. Simon G S. Evaluating chemical interaction studies for mixture risk assessment. *Human Ecological Risk Assessment* 7: 259-306, 2001.

Bowman K F, Monteiro-Riviere N A, Riviere J E. Development of surgical techniques for preparation of in vitro isolated perfused porcine skin flaps for percutaneous absorption studies. *Am. J. Vet. Res.* 52:75-82, 1991.

Bronaugh R. L. (ed.) Percutaneous absorption: drugs-cosmetics-mechanisms-methodology. 1999, Marcel Dekker, Inc. New York. Pp. 123

Bronaugh R L., Stewart R F, Congdonm E R, Giles A L. Methods for in vitro percutaneous absorption studies. I. Comparison with in vivo results. *Toxicol. Appl. Pharmacol.* 62: 481-488, 1982.

Brooks J D, Riviere J E. Quantitative percutaneous absorption and cutaneous distribution of binary mixtures of phenol and p-nitrophenol in isolated perfused porcine skin. *Fundam. Appl. Toxicol.* 32: 233-243, 1996.

Brown P J. Multivariate calibration. *J. Royal Stat. Soc. B* 44(3) 287-321, 1982.

Buchwald P, Bodor N. A simple, predictive, structure-based skin permeability model. *J. Pharm. Pharmacol.* 53: 1087-1098, 2001.

Budsaba K, Smith C E, Riviere J E. Compass Plots: A combination of star plot and analysis of means (ANOM) to visualize significant interactions in complex toxicology studies. *Toxicol. Methods* 10: 313-332, 2000.

Carver M P, Levi P E, Riviere J E. Parathion metabolism during percutaneous absorption in perfused porcine skin. *Pest. Biochem. Physiol.* 38:245-254, 1990.

Chang S K, Brooks J D, Monteiro-Riviere N A, Riviere J E. Enhancing or blocking effect of fenvalerate on the subsequent percutaneous absorption of pesticides in vitro. *Pest. Biochem. Physiol.* 51: 214-219, 1995.

Chang S K, Dauterman W C, Riviere J E. Percutaneous absorption of parathion and its metabolites paraoxon and p-nitrophenol administered alone or in combination: In Vitro flow through diffusion cell system. *Pest. Biochem. Physiol.* 48:56-62, 1994.

Chou C C, Riviere J E, Monteiro-Riviere N A. Differential relationship between the carbon chain length of jet fuel aliphatic hydrocarbons and their ability to induce cytotoxicity versus interleukin-8 release in human epidermal keratinocytes. *Toxicol. Sci.* 69: 226-233, 2002.

CRARM (Commission on Risk Assessment and Risk Management). U. S. Congress, Washington, D. C., 1997.

Cronin M T D, Dearden J C, Gupta R, Moss G P. An investigation of the mechanism of flux across polydimethylsiloxane membranes by use of quantitative structure-permeability relationships. *J. Pharm. Pharmacol.* 50: 143-152, 1998.

Cross S E, Pugh W J, Hadgraft J, Roberts M S. Probing the effect of vehicles on topical delivery. Understanding the basic relationship between solvent and solute penetration using silicone membranes. *Pharm. Res.* 18: 999-1005, 2001.

Denham M C, Brown P J. Calibration with many variables. *Appl. Statist.* 42(3): 515-528, 1993.

Dixit R, Riviere J E, Krishnan K, Andersen M E. Toxicokinetics and physiologically-based toxicokinetics in toxicology and risk assessment. *J. Toxicol Environ. Health Part B: Critical Reviews.* 6: 1-40, 2003.

El Tayar M, Tsai R S, Testa B, Carrupt P A, Hansch C, Leo A. Percutaneous penetration of drugs.: a quantitative structure-permeability relationship study. *J. Pharm. Sci.* 80: 744-749, 1991.

Elias P M. Epidermal lipids, barrier function and desquamation. *J. Invest. Dermatol.* 80: 44-49, 1983.

EPA (Environmental Protection Agency). *Guidelines for the Health Risk Assessment of Chemical Mixtures. Federal Register* 51: 34014-34025, September, 1986.

EPA. *Dermal Exposure Assessment: Principles and Applications.* EPA/600/8-91/011B, March, 1995.

EPA. *Options for Revising CEB's Method for Screen-Level Estimates of Dermal Exposure.* Chemical Engineering Branch, June, 2000.

EPA. *Technical Support Document on Risk Assessment of Chemical Mixtures*, EPA/600/8-90/064, November, 1988.

Feldstein M. M. Raigorodskii I. M. Iordanskii A. L. Hadgraft J. J. Controlled. Release 52(1998) 25-40.

Flynn G L, Yalkowski S H. Correlation and prediction of mass transport across membranes. I. Influence of alkyl chain length on flux-determining properties of barrier and diffusant. *J. Pharm. Sci.* 61: 838-857, 1972.

Flynn G L. Physicochemical determinants of skin absorption. In *Principles of Route-to-Route Extrapolation for Risk Assessment.* (Gerrity T R, Henry C J eds). Elsevier: New York, pgs. 93-127, 1990.

Frazier J M, Goldberg A M. Alternatives to and reduction of animal use in biomedical research, education and testing. *Altern. Lab. Anim.* 18: 65-74, 1990.

Geinoz S, Rey S, Boss G, Bunge A, Guy R H, Carrupt P A, Resit M, Testa B. Quantitative structure-permeation relationships for solute transport across silicone membranes. *Pharm. Res.* 19: 1622-1629, 2002.

Golden G M, McKie J E, Potts R O. The role of stratum corneum lipid fluidity in transdermal drug flux. *J. Pharm. Sci.* 76: 25-28, 1986.

Groton J P, Feron V J, Suhnel J. Toxicology of simple and complex mixtures. *TRENDS Pharmacol. Sci.* 22: 316-322, 2001.

Haddad S, Beliveau M, Tardif R, Krishnan K. A PBPK modeling-based approach to account for interactions in the health risk assessment of chemical mixtures. *Toxicol. Sci.* 63: 125-131, 2001.

Hansch C, Dunn W J. Linear relationships between lipophilic character and biological activity of drugs. *J. Pharm. Sci.* 61: 1-19, 1972.

Idson B. In vivo measurement of transepidermal water loss. *J. Soc. Cosmet. Chem.* 29: 573-580, 1978.

King J R, Monteiro-Riviere N A. Effects of organic solvent vehicles on the viability and morphology of isolated perfused porcine skin. *Toxicology* 69:11-26, 1991.

Kong R C, Fields S M, Jackson W P, Lee M L. Preparation of small-diameter capillary columns for gas and supercritical fluid chromatography. *J. Chromatogr.* 289:105-116, 1984.

Leahy D E. Intrinsic molecular volume as a measure of the cavity term in linear solvation energy relationships: Octanol-water partition coefficients and aqueous solubilities. *J. Pharm. Sci.* 75: 629-636, 1986.

Lotte C, Rougier A, Wilson D R, Maibach H I. In vivo relationship between transepidermal water loss and percutaneous penetration of some organic compounds in man: effect of anatomic site. *Arch. Dermatol. Res.* 279: 351-356, 1987.

Martin S D, Poole C F, Abraham M H. Synthesis and gas chromatographic evaluation of a high-temperature hydrogen-bond acid stationary phase. *J. Chromatogr. A,* 805: 217-235, 1998.

Martin T, Papich M, Riviere J E. Population pharmacokinetics of gentamicin in horses: A new approach to therapeutic drug monitoring and dose regimen determination in veterinary medicine: *Am. J. Vet. Res.* 59: 1589-1598, 1998.

Martin T, Riviere J E. Mixed effect modeling of the disposition of gentamicin across domestic animal species. *J. Vet. Pharmacol. Therap.* 24: 321-332, 2001.

Martin T, Riviere J E. Mixed effect modeling of the interspecies pharmacokinetic scaling of oxytetracycline. *J. Pharm. Sci.* 91: 331-341, 2002.

Martin T, Riviere J E. Population pharmacokinetics in veterinary medicine. Potential uses for therapeutic drug monitoring and prediction of tissue residues. *J. Vet. Pharmacol. Therap.* 21: 167-189, 1998.

Marx B D, Eilers P H C. Multivariate calibration stability: A comparison of methods. *J. Chemometrics* 16(3): 129-140, 2002.

McDougal J N, Robinson P J. Assessment of dermal absorption and penetration of components of a fuel mixture (JP-8). *Science Total Environ.* 288: 23-30, 2002.

Monteiro-Riviere N, Inman A, Riviere J. Effects of short-term high-dose and low-dose dermal exposure to jet A, JP-8 and JP-8+1000 jet fuels. *J. Appl. Toxicol.* 21: 485-494, 2001b.

Monteiro-Riviere N A, Baynes R E, Riviere J E. Pyridostigmine bromide modulates topical irritant-induced cytokine release from human epidermal keratinocytes and isolated perfused porcine skin. *Toxicology* 183: 15-28, 2003.

Monteiro-Riviere N A, Bowman K F, Scheidt V J, Riviere J E. The isolated perfused porcine skin flap (IPPSF): II. Ultrastructural and histological characterization of epidermal viability. *In Vitro Toxicol.* 1:241-252, 1987.

Monteiro-Riviere N A, Inman A O, Mak V, Wertz P, Riviere J E. Effects of selective lipid extraction from different body regions on epidermal barrier function. *Pharm. Res.* 18: 992-998, 2001a.

Monteiro-Riviere N A, Inman A O. Characterization of sulfur mustard-induced toxicity by enzyme histochemistry in porcine skin. *Toxicology Methods* 10:1-16, 2000.

Monteiro-Riviere N A. Anatomical Factors Affecting Barrier Function. In *Dermatotoxicology, 5th Edition* (F N Marzulli and H I Maibach eds), Taylor and Francis: Washington, D. C., pgs. 3-17, 1996

Monteiro-Riviere N A. Comparative Anatomy, Physiology, and Biochemistry of Mammalian Skin. In *Dermal and Ocular Toxicology: Fundamentals and Methods* (D W Hobson ed). CRC Press: Boca Raton. pgs. 3-71, 1991.

Monteiro-Riviere N A. Specialized Technique: Isolated Perfused Porcine Skin Flap. In *Methods for Skin Absorption* (B W Kemppainen and W G Reifenrath eds). CRC Press: Boca Raton. pgs. 175-189, 1990.

Moss G P, Dearden J C, Patel H, Cronin M T D. Quantitative structure-permeability relationships (QSPRs) for percutaneous absorption. *Toxicol. In Vitro* 16: 299-317, 2002.

Muhammad F, Baynes R E, Monteiro-Riviere N A, Xia X R, Riviere J E. Absorption Through Porcine Skin Exposed to Various Doses of Jet Fuel Marker Components Determined with GC-FID Using Head Space SPME Fiber. *Tox. Sci.* 71, 2003.

Pawliszyn J (ed). *Applications of Solid-Phase Microextraction*. The Royal Society of Chemistry: Hertfordshire, UK: 1999.

Peaden P A, Wright B W, Lee M L. The preparation of non-extractable methylphenylpolysiloxane stationary phases for capillary column gas chromatography. *Chromatographia*, 15: 335-340, 1982.

Poet T S, McDougal J N. Skin absorption and human risk assessment. *Chem. Biol. Interac.* 140: 19-34, 2002.

Pohl H R, Hansen H, Chou C H S J. Public health guidance values for chemical mixtures: Current practice and future directions. *Reg. Toxicol. Pharmacol.* 26: 322-329, 1997.

Potts R O, Golden G M, Franceour M L, Mak V H W, Guy R H. Mechanism and enhancement of solute transport across the stratum corneum. *J. Contr Release* 15: 249-260, 1991.

Potts R O, Guy R H. A predictive algorithm for skin permeability: The effects of molecular size and hydrogen bond activity. *Pharm. Res.* 12: 1628-1633, 1995.

Potts R O, Guy R H. Predicting skin permeability. *Pharm. Res.* 9: 663-669, 1992.

Pugh W J, Hadgraft J. Ab initio prediction of human skin permeability coefficients. *Int. J. Pharmaceut.* 103: 163-178, 1994.

Qiao G L, Brooks J D, Baynes R E, Monteiro-Riviere N A, Williams P L, Riviere J E. The use of mechanistically defined chemical mixtures (MDCM) to assess component effects on the percutaneous absorption and cutaneous disposition of topically-exposed chemicals. I. Studies with parathion mixtures in isolated perfused porcine skin. *Toxicology Appl. Pharmacol.* 141: 473-486, 1996.

Riviere J E, Baynes R E, Brooks J D, Yeatts J L, Monteiro-Riviere N A. Percutaneous absorption of topical diethyl-m-toluamide (DEET): Effects of exposure variables and coadministered toxicants. *J. Toxicol. Environ. Health. A.* 66: 133-151, 2003.

Riviere J E, Bowman K F, Monteiro-Riviere N A, Dix L P, Carver M P. The isolated perfused porcine skin flap. I. A novel in vitro model for percutaneous absorption and cutaneous toxicology studies. *Fund. Appl. Toxicol.* 7: 444-453, 1986.

Riviere J E, Brooks J D, Williams P L, Monteiro-Riviere N A. Toxicokinetics of topical sulfur-mustard penetration, disposition and vascular toxicity in isolated perfused porcine skin. *Toxicol. Appl. Pharmacol.* 135: 25-34, 1995.

Riviere J E, Brooks, J D, Williams P L, McGowan E, Francoeur M L. Cutaneous metabolism of isosorbide dinitrate after transdermal administration in isolated perfused porcine skin. *Int. J. Pharm.* 127: 213-217, 1996.

Riviere J E, Monteiro-Riviere N A, Baynes R E. Gulf War Illness-related exposure factors influencing topical absorption of $^{14}C$-permethrin. *Toxicol. Letters* 135: 61-71, 2002.

Riviere J E, Monteiro-Riviere N A, Brooks J D, Budsaba K, Smith C E. Dermal absorption and distribution of topically dosed jet fuels Jet A, JP-8, and JP-8(100). *Toxicol. Appl. Pharmacol.* 160: 60-75, 1999.

Riviere J E, Monteiro-Riviere N A, Williams P L. Isolated perfused porcine skin flap as an In Vitro model for predicting transdermal pharmacokinetics. *Eur. J. Pharm. Biopharm.* 41: 152-162, 1995.

Riviere J E, Monteiro-Riviere N A. The isolated perfused porcine skin flap as an in vitro model for percutaneous absorption and cutaneous toxicology. *Critical Reviews in Toxicol.* 21:329-344, 1991.

Riviere J E, Qiao G, Baynes R E, Brooks J D, Mumtaz M. Mixture component effects on the in vitro dermal absorption of pentachlorophenol. *Arch. Toxicol.* 75: 329-334, 2001b.

Riviere J E, Sage B S, Williams P L. The effects of vasoactive drugs on transdermal lidocaine iontophoresis. *J. Pharm. Sci.* 80:615-620, 1991.

Riviere J E, Smith C E, Budsaba K, Brooks J D, Olajos E J, Salem H, Monteiro-Riviere N A. Use of methyl salicylate as a stimulant to predict the percutaneous absorption of sulfur mustard. *J. Appl. Toxicol.* 21: 91-99, 2001 a.

Riviere J E, Williams P L, Hillman R, Mishky L. Quantitative prediction of transdermal iontophoretic delivery of arbutamine in humans using the in vitro isolated perfused porcine skin flap (IPPSF). *J. Pharm. Sci.* 81: 504-507, 1992.

Riviere J E. The isolated perfused porcine skin flap. In *Humane Innovations and Alternatives in Animal Experimentation: A Notebook.* (Bernstein E M ed). Psychologists for the Ethical Treatment of Animals: Saranac Lake, N. Y., pg 7, 1987.

Roberts M S, Anissimov Y G, Gonsalvez R A. Mathematical Models in Percutaneous Absorption. In *Percutaneous Absorption, 3rd Ed.* (Bronaugh R L, Maibach H I eds). Marcel Dekker: New York, pgs. 3-55, 1999.

Robinson P J. Prediction: Simple risk models and overview of dermal risk assessment. In *Dermal Absorption and Toxicity Assessment* (Roberts M S, Walters K A eds). Marcel Dekker: New York, pgs. 203-229, 1998.

S. Agatonovic-Kustrin, R. Beresford, A. P. M. Yusof, J. Pharm. Biomed. Anal. 26(2001)241-254.

Sartorelli P, Aprea C, Cenni A, Novelli M T, Orsi D, Palmi S, Matteucci G. Prediction of percutaneous Absorption from physiochemical data: A model based on data of in vitro experiments. *Ann. Occup. Hyg.* 42: 267-276, 1998.

Schaefer H. Redelmeier T. E. (eds) Skin barrier: principles of percutaneous absorption. 1996, S. Karger AG, Basel, Newzerland. Pp. 310.

Sheiner L B, Beal S L. Evaluation of methods for estimating population pharmacokinetic parameters. I. Michaelis-Menten model; routine clinical pharmacokinetic data. *J. Pharmacokin. Biopharm.* 8: 553-571, 1980.

Sheiner L B, Beal S L. Evaluation of methods for estimating population pharmacokinetic parameters. II. Monoexponential model; routine clinical pharmacokinetic data. *J. Pharmacokin. Biopharm.* 11: 303-319; 1981.

Sheiner L B, Beal S L. Evaluation of methods for estimating population pharmacokinetic parameters. III. Monoexponential model; routine clinical pharmacokinetic data. *J. Pharmacokin. Biopharm.* 11: 303-319, 1983.

Smith C E, Williams P L, Riviere J E. Compartmental models of skin transport: Dominant Eigenvalues approach. 1005 *Proc. Biometrics Section, Am. Statistical Assoc.* Pgs 449-454, 1996.

Spoo J W, Rogers R A, Monteiro-Riviere N A. Effects of formaldehyde, DMSO, benzoyl peroxide, and sodium lauryl sulfate on isolated perfused porcine skin. *In Vitro Toxicol.* 5: 251-260, 1992.

U. S. Pat. No. 5,576,217.
U. S. Pat. No. 5,691,206.
U. S. Pat. No. 6,042,787.
U. S. Pat. No. 6,164,144.

Walters K A. Penetration enhancers and their use in transdermal therapeutic systems. In *Transdermal Drug Delivery* (Hadgraft J, Guy R H eds). Marcel Dekker: New York, pgs. 197-246, 1989.

Wang Z, Xiao C, Wu C, Han H. High-performance polyethylene glycol-coated solid-phase microextraction fibers using sol-gel technology. *J. Chromatogr. A*, 893:157-168 (2000).

Wester R C, Maibach H I. Cutaneous pharmacokinetics: 10 steps to percutaneous absorption. *Drug Metab. Rev* 14: 169-205, 1983.

Wester R C, Melendres J, Sedik L, Maibach H I, Riviere J E. Percutaneous absorption of salicylic acid, theophylline, 2,4-dimethylamine, diethly hexylphthalic acid and ρ-aminobenzoic acid in the isolated perfused porcine skin flap compared to man. *Toxicol. Appl. Pharmacol.* 151: 159-165, 1998.

Wilhelm K P, Freitag G, Wolff H H. Surfactant-induced skin irritation and skin repair. *J. Am. Acad. Dermatol.* 30: 944-949, 1994.

Williams A C, Barry B W. Chemical penetration enhancement In *Dermal Absorption and Toxicity Assessment.* (Roberts M S, Walters K A eds). Marcel Dekker: New York, pgs. 297-312, 1998.

Williams P L, Carver M P, Riviere J E. A physiologically relevant pharmacokinetic model of xenobiotic percutaneous absorption utilizing the isolated perfused porcine skin flap (IPPSF). *J. Pharm. Sci.* 79: 305-311, 1990.

Williams P L, Riviere J E. A biophysically-based dermatopharmacokinetic compartment model for quantifying percutaneous penetration and absorption of topically applied agents. I. Theory. *J. Pharm. Sci.* 84: 599-608, 1995.

Williams P L, Riviere J E. A model describing transdermal iontophoretic delivery of lidocaine incorporating consideration of cutaneous microvascular state. *J. Pharm. Sci.* 82: 1080-1084, 1993.

Williams P L, Thompson D, Qiao G L, Monteiro-Riviere N A, Baynes R E, Riviere J E. The use of mechanistically defined chemical mixtures (MDCM) to assess component effects on the percutaneous absorption and cutaneous disposition of topically-exposed chemicals. II. Development of a general dermatopharmacokinetic model for use in risk assessment. *Toxicol. Appl. Pharmacol.* 141: 487-496, 1996.

Xia X R, Baynes R E, Monteiro-Riviere N A, Leidy R B, Shea D, Riviere J E. A novel in vitro technique for studying percutaneous permeation with a membrane coated fiber and gas chromatography/mass spectrometry. I.

Performance of the technique and determination of the permeation rates and partition coefficients of chemical mixtures. *Pharm. Res.* 20: 272-279, 2003a.

Xia X R, Baynes R E, Monteiro-Riviere N A, Riviere J E. A novel in vitro technique for studying percutaneous permeation with a membrane coated fiber and gas chromatography/mass spectrometry. II. Modeling permeation, diffusion and partition coefficients. *Pharm. Res.* (In Review, 2003b).

Xia X R, Leidy R B. Preparation and characterization of porous silica-coated multifibers for solid phase microextraction. *Anal. Chem.* 73: 2041-2047, 2001.

Yang R S H (ed). *Toxicology of Chemical Mixtures.* Academic Press: San Diego, 1994.

Zatz J L (ed). *Skin Permeation: Fundamentals and Applications.* Allured: Wheaton, Ill., 1993.

Zhang A, Riviere J E, Monteiro-Riviere N A. Topical sulfur mustard induces changes in prostaglandins and interleukin 1α in isolated perfused porcine skin. *In Vitro Toxicol* 8: 149-158, 1995.

It will be understood that various details of the invention may be changed without departing from the scope of the invention. Furthermore, the foregoing description is for the purpose of illustration only, and not for the purpose of limitation—the invention being defined by the claims.

What is claimed is:

1. A method of determining a molecular descriptor of absorption for a candidate compound, the method comprising:
   (a) providing a test solution comprising one or more candidate compounds;
   (b) immersing one or more simulated biological membranes into the test solution to partition the one or more candidate compounds into the membrane;
   (c) removing the one or more simulated biological membranes from the test solution and detecting the presence or amount of the one or more candidate compounds in the membrane at one or more permeation times; and
   (d) determining a molecular descriptor of absorption using the presence or amount of the one or more candidate compounds in the membrane at the one or more permeation times.

2. The method of claim 1, further comprising determining a plurality of molecular descriptors of absorption.

3. The method of claim 1, wherein the test solution comprises a plurality of test compounds.

4. The method of claim 1, comprising contacting the test solution with two or more simulated biological membranes to partition the one or more candidate compounds into the membranes.

5. The method of claim 4, comprising comparing the plurality of molecular descriptors of absorption to one or more reference molecular descriptors of absorption.

6. The method of claim 1, further comprising stirring the test solution during the contacting of step (b).

7. The method of claim 1, wherein the membrane comprises a material selected from the group consisting of:
   poly(methylsiloxane)(4-butanephenyl)-hexafluoropropan-2-ol, poly(dimethylsiloxane), poly(dimethylmethylphenylsiloxane)(10 mol % phenyl), poly(methylphenyldiphenylsiloxane)(75 mol % phenyl), poly(trifluoropropylmethylsiloxane), poly(methylphenylsiloxane), poly(cyanopropylmethyldimethylsiloxane), poly(cyanopropylmethylphenylmethylsiloxane), poly(ethylene glycol), poly(dimethylsiloxane)/carbowax copolymer, poly(dicyanoallylsiloxane), poly(diethylene glycol succinate), polydimethylsiloxane/divinylbenzene, carbowax/divinylbenzene, polyacrylate, copolymers thereof, and combinations thereof.

8. The method of claim 1, wherein the simulated biological membrane simulates a biological barrier or membrane selected from the group consisting of subcellular, cellular, oral/mucosal, gastrointestinal, blood-brain, respiratory-lung, nasal, ocular, subconjuctival, and skin.

9. The method of claim 1, wherein the detecting is done by gas chromatography or high performance liquid chromatography.

10. The method of claim 1, comprising comparing the molecular descriptor of absorption to a reference molecular descriptor of absorption.

11. The method of claim 1, wherein the detecting comprises desorbing the one or more candidate compounds from the membrane into an injector of a gas chromatograph or a high performance liquid chromatograph.

12. A method of determining a molecular descriptor of absorption for a candidate compound, the method comprising:
(a) providing a test solution comprising one or more candidate compounds;
(b) immersing one or more simulated biological membranes into the test solution to partition the one or more candidate compounds into the membrane, wherein the membrane is configured by one of disposing the membrane on a fiber or disposing the membrane within a tube;
(c) detecting the presence or amount of the one or more candidate compounds in the membrane at one or more permeation times; and
(d) determining a molecular descriptor of absorption using the presence or amount of the one or more candidate compounds in the membrane at the one or more permeation times.

13. The method of claim 12, wherein the membrane has a constant thickness along the fiber.

14. The method of claim 12, wherein the detecting is done by injecting the fiber into a gas chromatograph or high performance liquid chromatograph.

15. A method of determining a molecular descriptor of absorption for a candidate compound, the method comprising:
(a) providing a test system comprising:
(i) a membrane assembly comprising one of a fiber and a simulated biological membrane disposed thereon and a tube and a simulated biological membrane disposed therein; and
(ii) a container comprising a cover having one or more apertures disposed therein, the one or more apertures adapted to receive the membrane assembly;
(b) providing a test solution in the container, the test solution comprising one or more candidate compounds, wherein the one or more candidate compounds are present in a known concentration;
(c) immersing the simulated biological membrane into the test solution by placing the membrane assembly into an aperture of the container cover, whereby the one or more candidate compounds partition into the membrane;
(d) detecting the presence or amount of the one or more candidate compounds in the membrane at one or more permeation times; and
(e) determining a molecular descriptor of absorption using the presence or amount of the one or more candidate compounds in the membrane at the one or more permeation times.

16. The method of claim 15, further comprising determining a plurality of membrane absorption parameters.

17. The method of claim 15, wherein the test solution comprises a plurality of test compounds.

18. The method of claim 15, comprising contacting the test solution with two or more simulated biological membranes to partition the one or more candidate compounds into the membranes.

19. The method of claim 15, further comprising stirring the test solution during the contacting of step (c).

20. The method of claim 15, wherein the membrane comprises a material selected from the group consisting of:
poly(methylsiloxane)(4-butanephenyl)-hexafluoropropan-2-ol, poly(dimethylsiloxane), poly(dimethylmethylphenylsiloxane)(10 mol % phenyl), poly(methylphenyldiphenylsiloxane)(75 mol % phenyl), poly(trifluoropropylmethylsiloxane), poly(methylphenylsiloxane), poly(cyanopropylmethyldimethylsiloxane), poly(cyanopropylmethylphenylmethylsiloxane), poly(ethylene glycol), poly(dimethylsiloxane)/carbowax copolymer, poly(dicyanoallylsiloxane), poly(diethylene glycol succinate), polydimethylsiloxane/divinylbenzene, carbowax/divinylbenzene, polyacrylate, copolymers thereof, and combinations thereof.

21. The method of claim 15, wherein the membrane has a constant thickness along the fiber.

22. The method of claim 15, wherein the detecting is done by gas chromatography or high performance liquid chromatography.

23. The method of claim 22, wherein the detecting is done by injecting the fiber into a gas chromatograph or high performance liquid chromatograph.

24. The method of claim 15, wherein the one or more apertures are located at a fixed distance from a center point of the container.

25. The method of claim 24, wherein the fixed distance further comprises a fixed radius.

26. The method of claim 15, further comprising placing a plurality of membrane assemblies into the apertures of the container cover.

27. The method of claim 15, wherein the molecular descriptor of absorption is one of R, $\pi$, $\alpha$, $\beta$, V, and L, wherein R is an excess molar refraction, $\pi$ is an effective solute dipolarity and polarizability, $\alpha$ is an effective H-bond acidity, $\beta$ is an effective H-bond basicity, V is an intrinsic volume, and L is a gas-hexadecane partition coefficient at 25° C.

28. The method of claim 15, wherein the detecting comprises desorbing the one or more candidate compounds from the membrane into an injector of a gas chromatograph or a high performance liquid chromatograph.

29. A method of determining a molecular descriptor of absorption for a candidate compound, the method comprising:
(a) providing a test solution comprising one or more candidate compounds;
(b) immersing one or more simulated biological membranes into the test solution to partition the one or more candidate compounds into the membrane;
(c) detecting the presence or amount of the one or more candidate compounds in the membrane at one or more permeation times; and
(d) determining a molecular descriptor of absorption using the presence or amount of the one or more candidate compounds in the membrane at the one or more permeation times;
wherein the molecular descriptor of absorption is one of R, $\pi$, $\alpha$, $\beta$, V, and L, wherein R is an excess molar refraction, $\pi$ is an effective solute dipolarity and polarizability, $\alpha$ is an effective H-bond acidity, $\beta$ is an effective H-bond basicity, V is an intrinsic volume, and L is a gas-hexadecane partition coefficient at 25° C.

* * * * *